US007524643B2

(12) United States Patent
Qin et al.

(10) Patent No.: US 7,524,643 B2
(45) Date of Patent: *Apr. 28, 2009

(54) CDNA ENCODING THE HUMAN ALPHA2 DELTA4 CALCIUM CHANNEL SUBUNIT

(75) Inventors: Ning Qin, Blue Bell, PA (US); Ellen Codd, Blue Bell, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 1354 days.

This patent is subject to a terminal disclaimer.

(21) Appl. No.: 09/833,222

(22) Filed: Apr. 11, 2001

(65) Prior Publication Data

US 2003/0166045 A1 Sep. 4, 2003

(51) Int. Cl.
C12P 21/06 (2006.01)
C12Q 1/68 (2006.01)
C12N 15/00 (2006.01)
C12N 5/00 (2006.01)

(52) U.S. Cl. ...................... 435/69.1; 435/6; 435/320.1; 435/325; 536/23.1

(58) Field of Classification Search ....................... None
See application file for complete search history.

(56) References Cited

U.S. PATENT DOCUMENTS 6,013,474 A 1/2000 Brenner et al.

FOREIGN PATENT DOCUMENTS

| WO | WO 96/39512 A | | 12/1996 |
| WO | WO 00/20450 | * | 4/2000 |
| WO | WO 00/20450 A2 | | 4/2000 |
| WO | WO 01/08635 A | | 2/2001 |
| WO | WO 01/19870 A2 | * | 3/2001 |

OTHER PUBLICATIONS

Arikkath and Campbell, 2003, Current Opinion in Neurobiology 13:298-307.*
Qin et al., 2002. Mol Pharm. 62:485-496.*
Mickle JE et al., 2000. Med Clin North Am. 84:597-607.*
Voet et al. 1990. Bichemistry. John Wiley & Sons Inc., pp. 126-128 and 228-234.*
Yan et al., 2000. Science 290:523-527.*
Phillips AJ. 2001. Journal of Pharmacy and Pharmacology 53:1169-1174.*
Klugbauer N et al., 1999, Journal of Neuroscience 19:684-691.*
Bean et al., 1989. Classes of Calcium Channels in Vertebrate Cells. Annu. Rev. Physiol. 51:367-84.
Bertolino et al., 1992. The Central Role of Voltage-Activated and Receptor-Operated Calcium Channels in Neuronal Cells. Annu. Rev. Pharmacol. Toxicol. 32:399-421.
Birnbaumer et al., 1998. Structures and Functions of Calcium Channel β Subunits. Journal of Bioenergetics and Biomembranes. vol. 30(4): 357-375.
Castellano et al., 1993. Cloning and Expression of a Neuronal Calcium Channel β Subunits. The Journal of Biological Chemistry. vol. 268(17) Issue of Jun. 15, pp. 12359-12366.
Castellano et al., 1993. Cloning and Expression of a Third Calcium Channel β Subunits. The Journal of Biological Chemistry. vol. 268(5) Issue of Feb. 15, pp. 3450-3455.
Catterall. 1988. Structure and Function of Voltage-Sensitive Ion Channels. Science, 242:50-61.
D'Andrea et al., 1998. Characterization of Protease-activated Receptor-2 Immunoreactivity in Normal Human Tissues. The Journal of Histochemistry & Cytochemistry. 46(2):157-164.
Ellis et al., 1988. Sequence and Expression of mRNAs Encoding the $\alpha_1$ and $\alpha_2$ Subunits of a DHP-Sensitive Calcium Channel. Science. 241:1661-1664.
Ertel et al., 2000. Nomenclature of Voltage-Gated Calcium Channels. Neuron. 25:533-535.
Felex et al., 1997. Dissection of Functional Domains of the Voltage-Dependent $Ca^{2+}$ Channel $\alpha_2\delta$ Subunit. The Journal of Neuroscience. 17(18):6884-6891.
Gee et al., 1996. The Novel Anticonvulsant Drug, Gabapentin (Neurontin), Binds to the $\alpha_2\delta$ Subunit of a Calcium Channel. 271(10), Issue of Mar. 8, pp. 5768-5776.
Gilad et al., 1995. Identification of the alternative spliced form of the $\alpha_2/\delta$ subunit of voltage sensitive $Ca^{2+}$ Channels expressed in PC12 cells. Neuroscience Letters. 193:157-160.
Gurnett et al., 1996. Transmembrane auxiliary Subunits of Voltage-dependent Ion Channels. The Journal of Biological Chemistry. 271(45), Issue of Nov. 8, pp. 27975-27978.
Gurnett et al., 1996. Dual Function of the Voltage-Dependent $Ca^{2+}$ Channel $\alpha_2\delta$ Subunit in Current Stimulation and Subunit Interaction. Neuron. 16:431-440.
Hess, 1990. Calcium Channels in Vertebrate Cells. Annu. Rev. Neurosci. 13:357-56.
Hui et al., 1991. Molecular Cloning of Multiple Subtypes of a Novel Rat Brain Isoform of the $\alpha_1$ Subunit of the Voltage-Dependent Calcuim Channel. Neuron. 7:35-44.
Jay et al., 1990. Primary Structure of the γ Subunit of the DHP-Sensitive Calcium Channel from Skeletal Muscle. Science. 248:490-492.
Klugbauer et al., 1999. Molecular Diversity of the Calcium Channel $\alpha_2\delta$ Subunit. The Journal of Neuroscience. 19(2):684-691.
Kozak, 1991. An analysis of Vertebrate mRNA Sequences: Intimations of Translational Control. The Journal of Cell Biology. 115(4):887-903.
Lacerad et al., 1991. Normalization of current kinetics by interaction between the $\alpha_1$ and β subunits of the skeletal muscle dihydropyridine-sensitive $Ca^{2+}$ channel. Nature. 352:527-530.
Lee et al., 1999. Cloning and Expression of a Novel Member of the Low Voltage-Activated T-Type Calcium Channel Family. The Journal of Neuroscience. 19(6)1912-1921.

(Continued)

Primary Examiner—Manjunath Rao
Assistant Examiner—Shulamith H Shafer
(74) Attorney, Agent, or Firm—Yunling Ren

(57) ABSTRACT

The present invention provides nucleic acid and polypeptide sequences describing an isoform of the α2δ-4 subunit of a voltage gated calcium channel. The nucleic acids described herein can be used to produce functional α2δ-4 protein. The calcium channel α2δ-4 protein may be isolated for the purposes of binding experiments or may be used in cells to form a functional calcium channel complex.

7 Claims, 3 Drawing Sheets

OTHER PUBLICATIONS

Littleton et al., 2000. Ion Channels and Synaptic Organization: Analysis of the *Drosophila* Genome. Neuron. 26:35-43.

Mikami et al., 1989. Primary structure and functional expression of the cardiac dihydropyridine-sensitive calcium channel. Nature. 340:230-233.

Mori et al., 1991. Primary structure and functional expression from complementary DNA of a brain calcium channel. Nature. 350:398-402.

Perez-Reyes et al., 1989. Induction of calcium currents by the expression of the $\alpha_1$-subunit of the dihydropyridine receptor from skeletal muscle. Nature. 340:233-236.

Perez-Reyes et al., 1992. Cloning and Expression of a Cardiac/Brain $\beta$ Subunit of the L-type Calcium Channel. The Journal of Biological Chemistry. 267(3) Issue of Jan. 25, pp. 1792-1797.

Perez-Reyes et al., 1998. Molecular characterization of a neuronal low-voltage-activated T-type calcium channel. Nature 391:896-900.

Pragnell et al., 1991. Cloning and tissue-specific expression of the brain calcium channel $\beta$-subunit. Federation of European Biochemcial Societies. 291(2):253-258.

Qin et al., 1997. Direct interation of G$\beta\gamma$ with a C-terminal G$\beta\gamma$-binding domain of the $Ca^{2+}$ channel $\alpha_1$ subunit is responsible for channel inhibition by G protein-coupled receptors. Proc. Natl. Acad. Sci. USA. 94:8866-8871.

Qin et al., 1998. Modulation of human neuronal $\alpha_{1E}$-type calcium channel by $\alpha_2\delta$-subunit. American Physiological Society. 1324-1331.

Randall et al., 1995. Pharmacoogical Dissection of Multiple Types of $Ca^{2+}$ Channel Currents in Rat Cerebellar Granule Neurons. The Journal of Neurosciense. 15(4):2995-3012.

Rock et al., 1993. Gabapentin actions on ligand- and voltage-gated responses in cultured rodent neurons. Epilepsy Research. 16:89-98.

Ruth et al., 1989. Primary Structure of the $\beta$ Subunit of the DHP-Sensitive Calcium Channel from Skeletal Muscle. Science. 245:1115-1118.

Sanford et al., 1991. $\gamma$-Subunits of G Proteins, but not Their $\alpha$- or $\beta$-Subunits, are Polyisoprenylated. The Journal of Biological Chemistry. 266(15) Issue of May 25, pp. 9570-9579.

Snutch et al., 1990. Rat brain expresses a heterogeneous family of calcium channels. Proc. Natl. Acad. Sci. USA. Neurobiology. 87:3391-3395.

Tanabe et al., 1987. Primary structure of the receptor for calcuim channel blockers from skeletal muscle. Nature. 328:313-318.

Tanabe et al., 1988. Restoration of excitation-contraction coupling and slow calcium current in dysgenic muscle by dihydropyridine receptor complementary DNA. Nature. 336:134-139.

Tokumaru et al., 1995. A Calcium Channel from the Presynaptic Nerve Terminal of the *Narke japonica* Electric Organ Contains a Non-N-Type $\alpha_2\delta$ subunit. Journal of Neurochemistry. 65(2):831-836.

Williams et al., 1992. Structure and Functional Expression of an $\omega$-Conotoxin-Sensitive Human N-Type Calcium Channel Science. 257:389-395.

Wiser et al., 1996. The $\alpha 2/\delta$ subunit of voltage sensitive $Ca^{2+}$ Channels is a single transmembrane-extracellular protein which is involved in regulated secretion. FEBS Letters 379:15-20.

Witcher et al., 1993. Subunit Identification and Reconstitution of the N-Type $Ca^{2+}$ Channel Complex Purified from Brain. Science. 261:486-489.

Hosey et al., "L-Type Calcium Channels in Cardiac and Skeletal Muscle Purification and Phosphorylation" (1989) . An New York Academy of Sciences, 560. pp. 27-38.

Qin et al. 1998. "Modulation of Human Neuronal $\alpha_{1E}$-Type Calcium Channel by $\alpha_2\delta$-Subunit" American Physiological Society (Cell Physiology) 274. C1324-1331.

Brown, J.P. et. al: "Isolation of the 3HGABAPENTIN-Binding Protein/Alpha2Delta CA2+ Channel Subunit from Porcine Brain: Development of a Radiogiland Binding Assay for Alpha2delta Subunits using 2Hleucine" Analytical Biochemistry, Academic Press, San Diego, CA, US, vol. 255, No. 2 Jan. 15, 1998 pp. 236-243.

Catterall, W.A.: "Structure and Regulation of Voltage-gated Ca2+ Channels." Annual review of Cell and Developmental Biology. 2000 vol. 16, 2000, pp. 521-555.

Qin, Ning T. et. al: "Molecular Cloning and Characterization of the Human Voltage-Gated Calcium Channel Alpha (2) Delta-4 Subunit." Molecular Pharmacology. Sep. 2002 pp. 485-496.

Database EMBL *Homo sapiens* 12p13.3 PAC PRC15-1096D14, Aug. 4, 1998 XP002313810 retrieved from EMI Database Accession No. AC005342.

Database EMBL *Homo sapiens* Chromosome 12 Clone ROP11-76116, Mar. 17, 2001 XP002313811 retrieved from EBI Database accession No. AC090840.

Database EMBL *Homo sapiens* 12 BAC RP11-21K20, Aug. 4, 1998 XP002313812 retrieved from EBI Database Accession No. AC005343.

Database EMBL EST 7h46d04.X1, Dec. 15, 2000, XP 002313813 retrieved from EBI Database Accession No. BF590937.

EP Examination Report dated Aug. 22, 2005 for EP Application No. 02 728 726.7.

* cited by examiner

A: Fetal Liver

B: Gut (Paneth cells)

Figure 2 con't
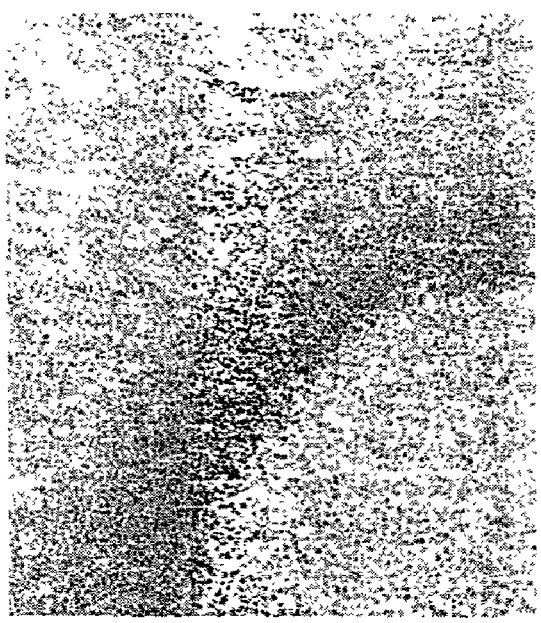
C: Tonsil
D: Cerebellum

CDNA ENCODING THE HUMAN ALPHA2 DELTA4 CALCIUM CHANNEL SUBUNIT

BACKGROUND OF THE INVENTION

Voltage gated calcium channels (VGCC or calcium channel) mediate $Ca^{2+}$ influx in excitable cells. Upon depolarization of the plasma membrane, calcium channels undergo a series of conformational changes that begin with charge movement resulting in the opening of a pore or conductance pathway that is selective for the influx of calcium ions (Catterall, W. A. (1988) *Science* 242:50-61 and Bean B P. (1989) *Annu. Rev. Physiol.* 51:367-368).

Calcium channels are a diverse class of proteins that have been traditionally separated into at least six different types based on their electrophysiological and pharmacological properties. The groups are referred to as L-type (for Long Lasting), T-type (for Transient), N-type (for neither L nor T, or for "Neuronal"), P-type (for Purkinje cell), Q-type and R-type (for resistant) Hess, (1990), *Ann. NY Acad. Sci.* 560: 27-38; Bertolino and Llinás, (1992) *Annu. Rev. Pharmacol. Toxicol.* 32:399-421; Randall and Tsien, (1995) *J. Neurosci.* 15:2995-3012). Except for the T type calcium channel, which is low voltage activated (LVA), the L-, N-, P-, Q- and R-types are all high voltage activated (HVA), i.e. their activation thresholds are normally above −40 mV.

The best characterized calcium channel is the rabbit skeletal muscle dihydropyridine (DHP)-sensitive L-type calcium channel. It is composed of four tightly associated subunits $\alpha_1$, $\alpha_2\delta$, $\beta$ and $\gamma$ (Catterall et al, supra, Hosey, et al. (1989) *Ann. N.Y. Acad. Sci.* 560:27-38). All of these subunits from rabbit have been characterized by molecular cloning (Tanabe et al, (1987) *Nature* 328:313-318; Ellis et al, (1988) *Science* 241: 1661-4; Ruth et al, (1989) *Science* 245: 1115-1118; and Jay et al, (1990) *Science* 248:490-492).

The neuronal conotoxin GVIA sensitive N-type calcium channel has also been purified (Witcher et al, (1993) *Science* 26:486-9). It contains $\alpha_{1B}$, $\alpha_2\delta$, and $\beta$ subunits but lacks a skeletal muscle-like $\gamma$ subunit. The $\alpha_1$ subunit cDNA clones of skeletal muscle L- and neuronal N-type calcium channel are termed $\alpha_{1S}$ and $\alpha_{1B}$, respectively. It has been shown that the $\alpha_1$ subunit alone can form a functional channel (Perez-Reyes et al, (1989) *Nature* 340:233-6 and Tanabe et al, (1988) *Nature* 336:134-139) while the $\alpha_2\delta$ and $\beta$ subunits play a regulatory role (Lacerda et al, (1991) *Nature* 352:527-530; Birnbaumer et al, (1998) *J. of Bioenergetics and Biomembranes* 30:357-375; and Qin et al, (1998) *Am. J. Physiol.* (*Cell Physiol.*), 274: C1324-C1331). The $\alpha_2\delta$ and $\beta$ subunits regulate almost all aspects of the channel properties including tight coupling between charge movement and pore opening, voltage dependent activation and inactivation, and prepulse potentiation.

To date, six non-allelic genes have been cloned encoding neuronal HVA-calcium channel $\alpha_1$ subunits (referred to as $\alpha_{1A}$ through $\alpha_{1F}$, and $\alpha_{1S}$) (Mikami et al, (1989) *Nature* 340:230-233; Snutch et al, (1990) *PNAS (USA)* 87;3391-395; Mori et al, (1991) *Nature* 350:398-402; Hui et al, (1991) *Neuron* 7:3-44; and Williams, (1992) *Science* 257:389-395) and three have been cloned encoding LVA-calcium channel $\alpha_1$ subunits ($\alpha_{1G}$-$\alpha_{1I}$) (Perez-Reyes et al, (1998) *Nature* 391: 896-900 and Lee et al, (1999) *J. Neurosci.* 19:1912-1921). Analyses of these sequences indicate that the primary sequences of the calcium channel cDNAs have homologies ranging from between 40%-70%. Hydropathicity analyses indicate that, like voltage-dependent sodium channels, calcium channel $\alpha_1$ subunits contain four homologous repeat transmembrane domains (domain I through IV). Each of these four domains contains five hydrophobic putative transmembrane spanning helices, referred to as S1-S3, S5 and S6, and one amphipathic segment (S4). The amphipathic segment contains highly-conserved, positively-charged amino acids every 3rd or 4th residue and this segment is thought to serve as the voltage sensor of the channel. The $\alpha_1$ subunit determines the functionality of the $Ca^{2+}$ channel ($\alpha_{1C}$, $\alpha_{1D}$ and $\alpha_{1F}$ for L-type, $\alpha_{1A}$ for P/Q-type, $\alpha_{1B}$ for N-type, $\alpha_{1E}$ most likely for R-type, and $\alpha_{1G}$ to $\alpha_{1I}$ for T-type).

Molecular cloning of calcium channels has also revealed that there are seven different types of $\alpha_1$ subunits for the (HVA) calcium channel, three types of $\alpha_2\delta$ subunits (Ellis et al, supra; Lugbauer et al, (1999) *J. Neurosci.* 19:684-691) and four types of $\beta$ subunits (Ruth et al, supra; Pragnell et al, (1991) *FEBS Lett.* 291:253-258; Perez-Reyes et al, (1992) *J. Biol. Chem.* 267:1792-1797) and Castellano et al, (1993) *J. Biol. Chem* 268:12359-12366 and Castellano et al. (1993) *J. Biol. Chem* 268: 3450-3455).

Recently, the analyses of *Drosophila* genomic sequences have revealed that there are four different types of $\alpha_1$, three types of $\alpha_2\delta$ and one type of $\beta$ subunit in *Drosophila* genome (Littleton and Ganetzhy, (2000) *Neuron* 26:35-43). Ten different mammalian $\alpha_1$ subunits have been identified. Based on the ratio of $\alpha_1$ and $\alpha_2\delta$ subunits (4 to 3) in Drosophila, there should be more than three types of $\alpha_2\delta$ subunits in mammals. No regulatory subunits of T-type channels ($\alpha_{1G}$ to $\alpha_{1H}$) have been identified yet, further suggesting that there are more VSCC subunits to be identified.

Understanding the molecular properties of the mature calcium channel subunits, their precursor proteins and the regulation of the calcium channel subunits require identification of a variety of calcium channel subunit nucleic acid sequences. An understanding of calcium channel subunit gene regulation is important for the identification of therapeutic agents affecting calcium channel function. Furthermore, the identification of a variety of nucleic acid sequences coding for calcium channel subunits is needed for the diagnosis of gene defects associated with calcium channel-implicated diseases.

A number of compounds useful in treating various diseases are thought to exert their beneficial effects by modulating voltage dependent calcium channel function. Many of these compounds bind to calcium channels and block or reduce the rate of $Ca^{2+}$ influx into cells in response to membrane depolarization. An understanding of the pharmacology of compounds that interact with calcium channels and the design of such compounds is limited by an understanding of the genes that code for them. Moreover, the identification of calcium channel subunits is needed to recombinantly produce sufficient quantities of highly purified channel subunits. With the availability of large amounts of purified calcium channel subunits, functional channels can be prepared and used in screening assays to identify or determine the effect of various compounds on channel function thereby providing a basis for the design of therapeutic agents which affect the calcium channel. Thus there is a need to further study the structure, subunit interaction, and channel composition of calcium channels.

A calcium channel $\alpha_2\delta$ subunit has been identified in every voltage-dependent calcium channel purified to date from various mammalian tissues including rabbit skeletal muscle and rabbit brain. Structurally, the $\alpha_2\delta$ subunit is a heavily glycosylated protein dimer that is encoded by a single gene and post-translationally cleaved to yield $\alpha_2\delta$ and $\delta$ subunits linked by a disulfide bond. Experimental evidence suggests a single transmembrane topology located in the $\delta$ subunit of the $\alpha_2\delta$ subunit (Gurnett, et al (1996) *Neuron* 16:431-40; Gurnett et al. (1996) *J. Biol. Chem.* 271:27975-8, and Felix, et al. (1997) *J. Neurosci.* 7:6884-910). The $\alpha_2\delta$ subunit regulates most of the properties of the calcium channels, including voltage dependent kinetics and ligand binding (Qin et al, supra).

Characterizing the effects of the calcium channel subunit on ligand binding demonstrated that the $\alpha_2\delta$ subunit alters the binding of neurological and cardiovascular drugs to the ion channel pore-forming $\alpha_1$ subunit. Recently, gabapentin, a novel anticonvulsant drug, was shown to bind with high affinity directly to the calcium channel $\alpha_2\delta$ subunit (Gee, et al. (1996) *J. Biol. Chem.* 271:5768-76). Gabapentin may control neuronal excitability by modifing calcium channel activity or expression (Rock et al, (1993) *Epilepsy Res.* 16:89-98). More interestingly, antibodies directed against the $\alpha_2\delta$ subunit block secretion from PC12 cells, suggesting that the $\alpha_2\delta$ subunit may play a distinct role in neurotransmitter release (Gilad et al (1995) *Neurosci. Lett.* 193:157-60; Tokumaru, et al. (1995) *J. Neurochem.* 65:831-836 and Wiser, et al. (1996) *FEBS Lett.* 379:15-20).

$Ca^{2+}$ ions play very important roles in normal cellular function including neurotransmitter release, cellular signaling, smooth and skeletal muscle contraction and gene expression. Regulation of intracellular $Ca^{2+}$ level is at the center of multiple systems for controlling numerous cellular functions. An abnormal intracellular $Ca^{2+}$ level is implicated in diseases such as neuropathic and chronic pain, migraine, Lambert-Eaton Syndrome, anxiety, seizures, epilepsy, ischemia, trauma, stroke Schizophrenia and Alzheimer's Disease as well as many other types of neuronal degeneration. Elevated or dysregulated $Ca^{2+}$ is also important in neuronal plasticity.

The defective $\alpha_2\delta$ gene has also been associated with proliferative diseases such as cancer and inflammation. Treatment with compounds that bind to $\alpha_2\delta$ to changes in the signal transduction mechanism of certain proteins including altered levels of MEK (MAP kinase kinase), an enzyme that activates the MAP kinase (mitogen-activated protein kinase). Inhibitors of MEK appear to mimic the analgesic activities associated with the binding of gabapentin to $\alpha_2\delta$. Activation of MAP kinase by mitogens appears to be essential for proliferation and constitutive activation of this kinase is sufficient to induce cellular transformation.

SUMMARY OF THE INVENTION

The present invention relates to DNA molecules and proteins encoding those molecules. The DNA molecules of this invention encode human $\alpha_2\delta$-4 calcium channel subunits. The subunit represents a novel isoform of the human calcium channel α2d protein. Functional DNA molecules encoding the channel subunit were isolated using a recombinant expression system. The biological and structural properties of the proteins encoded by the DNA molecules are disclosed. The recombinant DNA molecules and portions thereof, are useful for isolating homologues of the DNA molecules, identifying and isolating genomic equivalents of the DNA molecules, and identifying, detecting or isolating mutant forms of the DNA molecules. The recombinant protein is useful to identify modulators of the functional $\alpha_2\delta$-4 calcium channel subunit. In one aspect of the invention, the invention relates to isolated and purified nucleic acid molecule encoding an $\alpha 2\delta$-4 calcium channel subunit protein, said nucleic acid molecule comprising a member selected from the group consisting of: (a) a nucleic acid molecule encoding a protein having at least a 95% identity to a polypeptide comprising amino acids 1 to 1090 of SEQ ID NO:10; (b) a nucleic acid molecule that is complementary to the polynucleotide of (a); (c) a nucleic acid molecule comprising at least 15 sequential bases of the polynucleotide of (a) or (b); (d) a nucleic acid molecule that hybridizes under stringent conditions to the polynucleotide molecule of (a) and has at least a 95% identity to the nucleic acid encoding a polypeptide comprising amino acids 1 to 1090 of SEQ ID NO:10; (e) a nucleic acid molecule that encodes a splice variant of a human alpha 2 calcium channel comprising exon 1B; (f) a nucleic acid molecule that encodes a splice variant of a human alpha 2 calcium channel comprising exon 37B; and (g) a nucleic acid molecule that encodes a splice variant of a human alpha 2 calcium channel comprising exon 1B and exon 37B. In one embodiment, the nucleic acid molecule can be RNA or DNA. In another embodiment the nucleotide has the nucleotide sequence of (SEQ.ID.NO.:9).

The invention further relates to an expression vector to express an α2δ-4 calcium channel subunit protein in a recombinant host, wherein the vector contains a nucleic acid sequence encoding a α2δ-4 calcium channel subunit protein. Preferably the vector contains a nucleic acid molecule encoding an α2δ-4 calcium channel subunit protein having at least a 95% identity to a polypeptide comprising amino acids 1 to 1090 of SEQ ID NO:10. The invention further relates to the expression vector in a recombinant host cell. Preferably recombinant host cell comprises a nucleic acid molecule having a nucleotide sequence encoding an α2δ-4 calcium channel subunit protein having at least a 95% identity to a polypeptide comprising amino acids 1 to 1090 of SEQ ID NO:10.

In another aspect of this invention, the invention relates to a protein, in substantially pure, form having at least a 95% identity with a polypeptide comprising amino acids 1-1090 of SEQ ID NO.:10. In one embodiment, this protein has an amino acid sequence of: SEQ.ID.NO.:10.

The invention further relates to monospecific antibody immunologically reactive with an α2δ-4 calcium channel subunit protein. Preferably the antibody blocks activity of the α2δ-4 calcium channel subunit protein.

The invention also includes a method for expressing an α2δ-4 calcium channel subunit protein in a recombinant host cell, comprising the steps of: (a) transferring an expression vector capable of encoding an α2δ-4 calcium channel subunit protein into a cell; and (b) culturing the cells under conditions that allow expression of the α2δ-4 calcium channel subunit protein from the expression vector.

A method for identifying compounds that alter α2δ-4 calcium channel subunit protein activity in a cell is also included in this invention. This invention comprises the steps of: a) contacting a compound with a cell containing an α2δ-4 calcium channel subunit, and b) measuring a change in the cell in response to the contacting step. In one embodiment, the cell contains three additional calcium channel subunits: an alpha2 subunit, a beta subunit, and a gamma subunit; and wherein the three subunits and the α2δ-4 subunit form a calcium channel complex. Preferably the calcium channel complex is an L-type Voltage Sensitive Calcium Channel and the measuring step is measuring the influx of $Ca^{2+}$ into the cell.

The invention further relates to a method comprising the steps of: (a) incubating a cell membrane from a cell expressing recombinant α2δ-4 with radioactive gabapentin (GBP) and a candidate compound, wherein the membrane comprises an α2δ-4 subunit of calcium channel and wherein the incubating step is for sufficient time to allow GBP binding to the α2δ-4 subunit of calcium channels in the cell membranes, (b) separating the cell membranes from unbound radioactive GBP, (c) measuring binding of the radioactive GBP to the cell membranes, and (d) identifying a compound that inhibits GBP binding by a reduction of the amount of radioactive GBP in step (c) to an established control.

In another aspect of this invention, the invention relates to a method for identifying compounds that alter α2δ-4 calcium channel subunit protein activity, comprising the steps of: (a) combining a compound, a measurably labeled ligand for the α2δ-4 calcium channel subunit protein, and a α2δ-4 calcium channel subunit protein, and (b) measuring binding of the compound to the subunit protein by a reduction in the amount labeled ligand binding to the α2δ-4 calcium channel subunit protein.

The invention further relates to compounds active in these methods where the compound is an agonist or antagonist of an α2δ-4 calcium channel. Preferably the compound is a modulator of expression of a α2δ-4 calcium channel subunit.

The invention further relates to a pharmaceutical composition comprising a compound active in a method for identifying compounds that alter α2δ-4 calcium channel subunit protein activity.

DETAILED DESCRIPTION

Definitions

Figure 1:
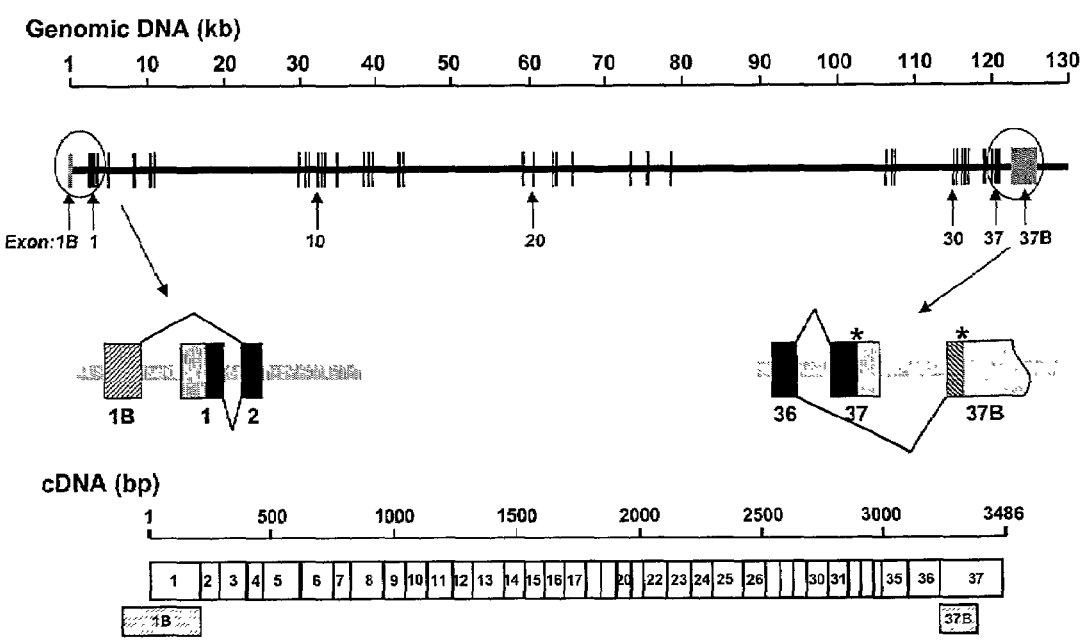
FIG. 1 illustrates the genomic structure of the human calcium channel $\alpha_2\delta$-4 subunit.
Figure 2:
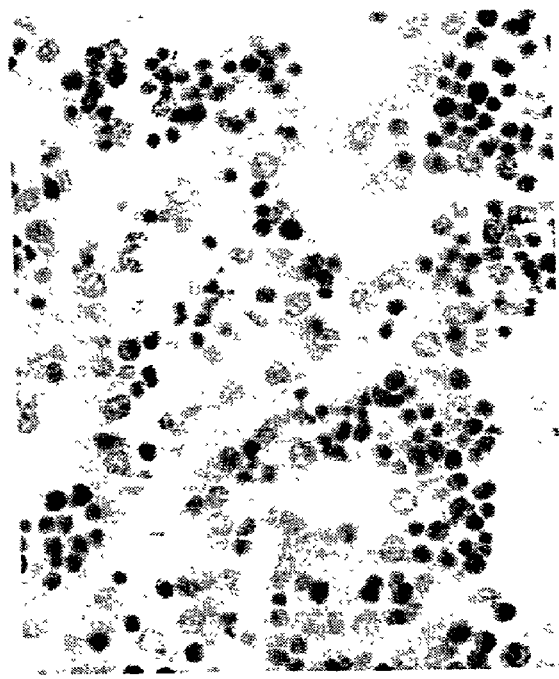
FIG. 2 illustrates exemplary immunohistochemical analyses of $Ca^{2+}$ channel $\alpha_2\delta$-4 subunit protein expression in human tissues. A: Fetal liver, B. Gut (paneth cells), C. Tonsil and D. Cerebellum.
Figure 2:
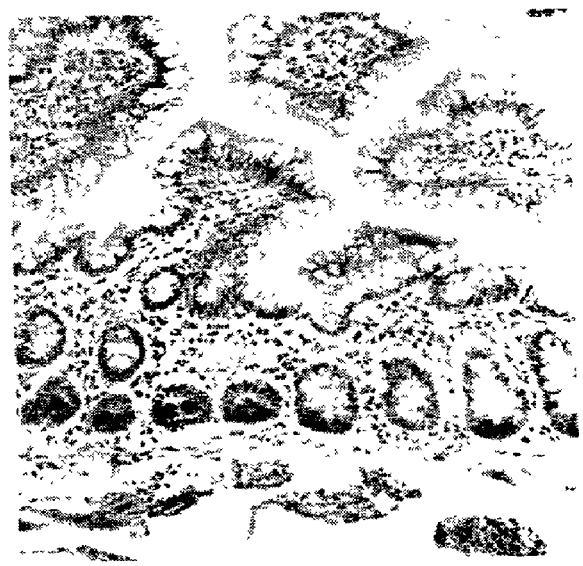

The term "protein domain" as used herein refers to a region of a protein having a particular three-dimensional structure that has functional characteristics independent from the remainder of the protein. This structure may provide a particular activity to the protein. Exemplary activities include, without limitation, enzymatic activity, creation of a recognition motif for another molecule, or to provide necessary structural components for a protein to exist in a particular environment. Protein domains are usually evolutionarily conserved regions of proteins, both within a protein family and within protein superfamilies that perform similar functions.

The term "protein superfamily" as used herein refers to proteins whose evolutionary relationship may not be entirely established or may be distant by accepted phylogenetic standards yet show similar three dimensional structure or display a unique consensus of critical amino acids.

The term "protein family" as used herein refers to proteins whose evolutionary relationship has been established by accepted phylogenic standards.

The term "fusion protein" as used herein refers to protein constructs that are the result of combining multiple protein domains or linker regions. Fusion proteins can be created for the purpose of gaining the combined functions of the domains or linker regions. Fusion proteins can be created by molecular cloning of the nucleotide sequences to generate a contiguous nucleotide sequence encoding the fusion protein. Alternatively, creation of a fusion protein may be accomplished by chemically joining two proteins.

The term "linker region" or "linker domain" or similar such descriptive terms as used herein refers to one or more polynucleotide or polypeptide sequences that are used in the construction of a cloning vector or fusion protein. The function of a linker region can include introduction of cloning sites into the nucleotide sequence, introduction of a flexible component or space-creating region between two protein domains, or creation of an affinity tag to facilitate a specific molecule interaction. A linker region may be introduced into a fusion protein, if desired, during polypeptide or nucleotide sequence construction.

The term "cloning site" or "polycloning site" as used herein refers to a region of the nucleotide sequence that has one or more available restriction endonuclease consensus cleavage sequences. These nucleotide sequences may be used for a variety of purposes including, but not limited to, introduction of these sequences into DNA vectors to create novel fusion proteins, or to introduce specific site-directed mutations. It is well known by those of ordinary skill in the art that cloning sites can be engineered at a desired location by silent mutation, conserved mutation, or introduction of a linker region that contains desired restriction endonuclease recognition sequences. It is also well known by those of ordinary skill in the art that the precise location of a cloning site can be engineered into any location in a nucleotide sequence.

The term "tag" as used herein refers to an amino acid sequence or a nucleotide sequence that encodes an amino acid sequence that facilitates isolation, purification or detection of a protein containing the tag. A wide variety of such tags are known to those skilled in the art and are suitable for use in the present invention. Suitable tags include, but are not limited to, HA peptide, polyhistidine peptides, biotin/avidin, and a variety of antibody epitope binding sites.

Isolation of Human Voltage Gated Calcium Channel $\alpha_2\delta$-4 Subunit Nucleic Acid The voltage gated calcium channel is a multi-subunit protein complex containing a pore forming subunit $\alpha_1$, and two regulatory subunits, $\alpha_2\delta$ and $\beta$. While the $\alpha$ subunit determines the basic properties of the channel, the $\alpha_2\delta$ and $\beta$ subunits modulate almost all aspects of the channel properties including voltage dependent gating, voltage dependent activation and inactivation, as well as increasing functional channel density on the membrane. From molecular pharmacologic and electrophysiologic perspectives, there are more subtypes of voltage gated calcium channels in the excitable cells than there are cloned $\alpha_1$ subunits. This is due in part to the existence of more than one $\alpha$ subunit protein. On the other hand, one might also expect that there is more than one type of $\alpha_2\delta$ and $\beta$ subunit. In other words, the variety of voltage gated calcium channels may result from the different combinations of $\alpha_1$, $\alpha_2\delta$ and $\beta$ subunits.

The present invention relates to novel DNA encoding a calcium channel $\alpha_2\delta$-4 subunit isolated from $\alpha_2\delta$-4 calcium channel subunit producing cells. Neither the complete amino acid sequence nor the nucleic acid sequence of a calcium channel $\alpha_2\delta$-4 subunit was known previously. It is predicted that a wide variety of cells and cell types will contain calcium channel $\alpha_2\delta$-4 subunit channel subunit as described herein. Vertebrate cells naturally expressing the calcium channel $\alpha_2\delta$-4 subunit include, but are not limited to, brain, heart and skeletal muscles. These cells and others naturally expressing the subunit can be used for $\alpha_2\delta$-4 subunit cDNA isolation.

Other cells and cell lines may also be used to isolate calcium channel $\alpha_2\delta$-4 subunit cDNA. The selection of other cells may be made after screening for calcium channel $\alpha_2\delta$-4 subunit activity in cell extracts or in whole cell assays, described herein. Cells that possess calcium channel $\alpha_2\delta$-4 subunit activity in these assays may be suitable for the isolation of calcium channel $\alpha_2\delta$-4 subunit DNA or mRNA.

Any of a variety of procedures known in the art may be used to clone calcium channel $\alpha_2\delta$-4 subunit DNA. One method is to direct functional expression of the calcium channel $\alpha_2\delta$-4 subunit genes following the construction of a calcium channel $\alpha_2\delta$-4 subunit-containing cDNA library in an appropriate expression vector system. Another method is to screen a calcium channel $\alpha_2\delta$-4 subunit-containing cDNA library constructed in a bacteriophage or plasmid shuttle vector with a labelled oligonucleotide probe designed from all or part of the amino acid sequence of the calcium channel $\alpha_2\delta$-4 subunit. An additional method includes screening a calcium channel $\alpha_2\delta$-4 subunit-containing cDNA library constructed in a bacteriophage or plasmid shuttle vector with a partial cDNA encoding the calcium channel $\alpha_2\delta$-4 subunit protein. This partial cDNA is obtained using specific PCR amplification of the calcium channel $\alpha_2\delta$-4 subunit DNA fragments through the design of degenerate oligonucleotide primers from the amino acid sequence of the purified calcium channel $\alpha_2\delta$-4 subunit protein.

Yet another method is to isolate RNA from calcium channel $\alpha_2\delta$-4 subunit-producing cells and translate the RNA into protein via an in vitro or an in vivo translation system. The translation of the RNA into a peptide or a protein will result in the production of at least a portion of the calcium channel $\alpha_2\delta$-4 subunit protein. This protein can then be identified by, for example, immunological reactivity with an anti-calcium channel $\alpha_2\delta$-4 subunit antibody or by biological activity of calcium channel $\alpha_2\delta$-4 subunit protein such as by measuring calcium influx or gabapentin binding to the $\alpha_2\delta$ subunit. Alternatively, pools of RNA isolated from calcium channel $\alpha_2\delta$-4 subunit-producing cells can be analyzed for the presence of an RNA that encodes at least a portion of the calcium channel $\alpha_2\delta$-4 subunit protein. Further fractionation of the RNA pool can be performed to purify the calcium channel $\alpha_2\delta$-4 subunit RNA from non-calcium channel $\alpha_2\delta$-4 subunit RNA. The peptide or protein produced by this method may be analyzed to provide amino acid sequences, which in turn are used to provide primers for the production of calcium channel $\alpha_2\delta$-4 subunit cDNA. The RNA that was used for translation can be analyzed to provide nucleotide sequences encoding a calcium channel $\alpha_2\delta$-4 subunit and produce probes for the production of calcium channel $\alpha_2\delta$-4 subunit cDNA. This method is known in the art and can be found in, for example, Maniatis, T., Fritsch, E. F., Sambrook, J. in *Molecular Clonina: A Laboratory Manual*, Second Edition, Cold Spring Harbor Laboratory Press, Cold Spring Harbor, N.Y. 1989.

It is readily apparent to those skilled in the art of molecular biology that other types of libraries, as well as libraries constructed from other cells or cell types, may be useful for isolating calcium channel $\alpha_2\delta$-4 subunit-encoding DNA. Other types of libraries include, but are not limited to, cDNA libraries derived from other cells, libraries derived from a variety of organisms expressing other calcium channel $\alpha_2\delta$-4 subunits, and from genomic DNA libraries that include YAC (yeast artificial chromosome) and cosmid libraries.

The selection of cells or cell lines for use in preparing a cDNA library to isolate calcium channel $\alpha_2\delta$-4 subunit cDNA may be performed by first measuring cell associated calcium channel $\alpha_2\delta$-4 subunit activity using the measurement of calcium channel $\alpha_2\delta$-4 subunit-associated biological activity or using a ligand binding assay.

Preparation of cDNA libraries can be performed by standard techniques well known in the art. Well known cDNA library construction techniques can be found for example, in Maniatis, T., et al., supra. It is also readily apparent to those skilled in the art that DNA encoding a calcium channel $\alpha_2\delta$-4 subunit may be isolated from a suitable genomic DNA library.

Construction of genomic DNA libraries can be performed by standard techniques well known in the art. Well known genomic DNA library construction techniques are also found in Maniatis, T., et al., supra.

In order to clone the calcium channel $\alpha_2\delta$-4 subunit gene by the above methods, knowledge of the amino acid sequence of calcium channel $\alpha_2\delta$-4 subunit may be required. Calcium channel $\alpha_2\delta$-4 subunit protein may be purified and partial amino acid sequences determined by automated sequenators. It is not necessary to determine the entire amino acid sequence, but the linear sequence of two regions of 6 to 8 amino acids from the protein can be determined for the production of primers for PCR amplification of a partial calcium channel $\alpha_2\delta$-4 subunit DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the calcium channel $\alpha_2\delta$-4 subunit sequence but will, under the appropriate hybridization conditions, be able to hybridize to calcium channel $\alpha_2\delta$-4 subunit DNA. DNA isolated by these methods can be used to screen DNA libraries from a variety of cell types, from invertebrate and vertebrate sources, and to isolate homologous genes.

The purified biologically active calcium channel $\alpha_2\delta$-4 subunit may have several different physical forms. The calcium channel $\alpha_2\delta$-4 subunit may exist as a full-length nascent or unprocessed polypeptide, or as partially processed polypeptides or combinations of processed polypeptides. The full-length nascent calcium channel $\alpha_2\delta$-4 subunit polypeptide may be post-translationally modified by specific proteolytic cleavage events resulting in the formation of fragments of the full length nascent polypeptide. A fragment or physical association of fragments may have the full biological activity associated with the calcium channel $\alpha_2\delta$-4 subunit; however, the degree of calcium channel $\alpha_2\delta$-4 subunit activity may vary between individual calcium channel $\alpha_2\delta$-4 subunit fragments and physically associated calcium channel $\alpha_2\delta$-4 subunit polypeptide fragments.

Because the genetic code is degenerate, more than one codon may be used to encode a particular amino acid. Therefore, the amino acid sequence can be encoded by any of a set of similar DNA oligonucleotides. Only one member of the set will be identical to the calcium channel $\alpha_2\delta$-4 subunit sequence but will be capable of hybridizing to calcium channel $\alpha_2\delta$-4 subunit DNA even in the presence of DNA oligonucleotides with mismatches under appropriate conditions. Under alternate conditions, the mismatched DNA oligonucleotides may still hybridize to the calcium channel $\alpha_2\delta$-4 subunit DNA to permit identification and isolation of calcium channel $\alpha_2\delta$-4 subunit encoding DNA.

DNA encoding a calcium channel $\alpha_2\delta$-4 subunit from a particular organism may be used to isolate and purify homologues of calcium channel $\alpha_2\delta$-4 subunits from other organisms. To accomplish this, the first calcium channel $\alpha_2\delta$-4 subunit DNA can be used to hybridize with a sample containing DNA that encodes homologous calcium channel $\alpha_2\delta$-4 subunits under appropriate hybridization conditions. The hybridized DNA complex may be isolated and the DNA encoding the homologous DNA can then be purified.

Functional Derivatives/Variants

There is a substantial amount of redundancy in the various codons that code for specific amino acids. Therefore, this invention is also directed to those DNA sequences that contain alternative codons that code for the translation of the identical amino acid. For purposes of this specification, a nucleic acid sequence having one or more codons that vary yet still encode an identical amino acid sequence will be defined as a degenerate variation. Nucleic acid sequences with degenerate variations are contemplated within the scope of this invention.

Also included within the scope of this invention are sequences that include mutations either in the DNA sequence or the translated protein, which do not substantially alter the ultimate physical properties of the expressed protein. For example, substitution of aliphatic amino acids alanine, valine, leucine and isoleucine; interchange of the hydroxyl residues serine and threonine; exchange of the acidic residues aspartic acid and glutamic acid; substitution between the amide residues asparagine and glutamine; exchange of the basic residues lysine and arginine; and substitution among the aromatic residues phenylalanine and tyrosine may not cause a change in functionality of the polypeptide. Such substitutions are well known and are described, for instance in *Molecular Biology of the Gene*, 4th Ed. Bengamin Cummings Pub. Co. by Watson et al.

It is known that DNA sequences coding for a peptide may be altered to code for peptides having properties that are different from those of the naturally occurring peptide. Methods of altering DNA sequences include, but are not limited to, site directed mutagenesis, chimeric substitution, and gene fusion. Site-directed mutagenesis is used to change one or more DNA residues that may result in a silent mutation, a conservative mutation, or a nonconservative mutation. Chimeric genes can be prepared by replacing domains within the calcium channel $\alpha_2\delta$-4 subunit gene with domains from similar or different genes. Fusion genes may be prepared by adding domains or gene fragments from other genes to the calcium channel $\alpha_2\delta$-4 subunit gene. Examples of fusion genes include genes encoding a protein containing an affinity tag to facilitate identification and isolation of the fusion gene or of the resulting protein. Fusion genes may be prepared by creating a soluble version of the protein by, for example, removing one or more transmembrane domains or by adding a targeting sequence to redirect the normal transport of the protein. Alternatively, fusion genes can be prepared that add new post-translational modification sequences to the calcium channel $\alpha_2\delta$-4 subunit gene. Examples of altered properties include, but are not limited to, changes in the affinity of an enzyme for a substrate or a receptor for a ligand. All of these changes can be used to create useful variants of the present invention so long as the original function (i.e., the ability of the subunit gene to form a functional calcium channel) of the polynucleotide or polypeptide sequence of the present invention is maintained as described herein.

Identity or similarity, as known in the art, refers to the relationship between two or more polypeptide sequences or two or more polynucleotide sequences as determined by comparing the sequences. In the art, identity also refers to the degree of sequence relatedness between polypeptide or polynucleotide sequences, as the case may be, as determined based on the extent of matches between strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exists a number of methods to measure identity and similarity between two polynucleotide or two polypeptide sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., (1988) *SIAM J. Applied Math.*, 48, 1073. Methods commonly employed to determine identity or similarity between sequences include, but are not limited to, those disclosed in Carillo, H., and Lipman, D., supra. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) *Nucleic Acids Research* 12(1), 387), BLASTP, BLASTN, and FASTA (Atschul, S. F. et al., (1990) *J. Molec. Biol.* 215, 403).

The term "polynucleotide(s)" as used herein refers to any polyribonucleotide or polydeoxribonucleotide which may be unmodified RNA or DNA or modified RNA or DNA. Thus polynucleotides, as used herein, refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein also refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including both eukaryotic and prokaryotic cells. The term "polynucleotides" further is used herein to include short polynucleotides often referred to as oligonucleotide(s).

The term polypeptides, as used herein, refers to the basic chemical structure of polypeptides that is well known and has been described in textbooks and other publications in the art, In this context, the term is used herein to refer to any peptide, polypeptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature and they are well known to those of skill in the art.

The polypeptides of the present invention may include known modifications such as acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in this art and have been described in great detail in the scientific literature. Several particularly common modifications including, but not limited to, glycosylation, lipid attachment, sulfation, gamma-carboxylation of glutamic acid residues, hydroxylation and ADP-ribosylation are described in most basic texts, such as, for example *Proteins—Structure and Molecular Properties,* 2nd Ed., T. E. Creighton, W. H. Freeman and Company, New York (1993). Many detailed reviews are available on this subject, such as, for example, those provided by Wold, F., Post-translational Protein Modifications: Perspectives and Prospects, pgs. 1-12 in *Post-translational Covalent Modification of Proteins*, B. C. Johnson, Ed., Academic Press, New York (1983); Seifter et al., (1990) *Meth. Enzymol.* 182: 626-646 and Rattan et al., "Protein Synthesis: Posttranslational Modifications and Aging", (1992) *Ann. N.Y. Acad. Sci.* 663: 48-62.

It will be appreciated, as is well known and as noted above, that polypeptides are not always entirely linear. For instance, the term "polypeptide" further includes molecules that may not occur naturally, but may be the product of, for example, post-translational events or further human manipulation. Examples of these polypeptides include circular, branched and branched circular polypeptides that can be synthesized by non-translation natural processes and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For example, the amino terminal residue of polypeptides made in *E. coli* or other cells, prior to proteolytic processing will almost invariably be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention.

The modifications that occur in a polypeptide often will be a function of how it is made. For polypeptides made by expressing a cloned polynucleic acid sequence in a host, for instance, the nature and extent of the modifications in large part will be determined by the host cell posttranslational modification capacity and the modification signals present in the polypeptide amino acid sequence. For example, as is well known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

The term "variant(s)" as used here in refers to polynucleotides or polypeptides that differ from a reference polynucleotide or polypeptide, respectively. A variant of a polynucleotide may be a naturally occurring variant such as a naturally occurring allelic variant or it may be a variant that is not known to occur naturally.

Polynucleotide variants are those that differ in nucleotide sequence from another reference polynucleotide. Generally, differences are limited so that the nucleotide sequences of the reference and the variant are closely similar overall and, in many regions, identical. As noted below, changes in the nucleotide sequence of the variant may be silent. That is, the change may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above.

A polypeptide variant refers to polypeptides that differ in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of an $\alpha 2 \delta 4$ calcium channel subunit is a compound that possesses a biological activity (either functional or structural) that is substantially similar to the biological activity of the $\alpha 2\delta$-4 calcium channel subunit provided in SEQ ID NO:10. The term "functional derivatives" is intended to include the "fragments," "variants," "degenerate variants," "analogs" and "homologues" or to "chemical derivatives" of calcium channel $\alpha_2\delta$-4 subunits. Useful chemical derivatives of polypeptides are well known in the art and include, for example covalent modification of one or more reactive organic sites contained within the polypeptide with a secondary chemical moiety. Well known cross-linking reagents are useful to react to amino, carboxyl, or aldehyde residues to introduce, for example an affinity tag such as biotin, a fluorescent dye, or to conjugate the polypeptide to a solid phase surface (for example to create an affinity resin).

The term "fragment" is meant to refer to any polypeptide subset of a calcium channel $\alpha_2\delta$-4 subunit. A molecule is "substantially similar" to a calcium channel $\alpha_2\delta$-4 subunit if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire calcium channel $\alpha_2\delta$-4 subunit molecule or to a fragment thereof.

Particularly preferred polynucleotides of this invention encode variants, analogs, derivatives and fragments of SEQ.ID.NO.:9, and variants, analogs and derivatives of the fragments, which have the amino acid sequence of the polypeptide of SEQ.ID.NO.:10 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the protein encoded by the nucleic acid of SEQ.ID.NO.:9. Also especially preferred in this regard are conservative substitutions. Most highly preferred are polynucleotides encoding polypeptides having the amino acid sequence of SEQ.ID.NO.:10, without substitutions.

Further preferred embodiments of the invention are polynucleotides that are at least 70% identical over their entire length to a polynucleotide encoding the polypeptide having the amino acid sequence set out in SEQ.ID.NO.:10, and polynucleotides which are complementary to such polynucleotides. Alternatively, highly preferred are polynucleotides that comprise a region that is at least 80% identical, more highly preferred are polynucleotides that comprise a region that is at least 90% identical, and among these preferred polynucleotides, those with at least 95% are especially preferred. Furthermore, those with at least 97% identity are highly preferred among those with at least 95%, and among these those with at least 98% and at least 99% are particularly highly preferred, with at least 99% being the most preferred. The polynucleotides which hybridize to the above described polynucleotides in a preferred embodiment encode polypeptides which retain substantially the same biological function or activity as the polypeptide characterized by the deduced amino acid sequence of SEQ.ID.NO.:10. Preferred embodiments in this respect, moreover, are polynucleotides that encode polypeptides that retain substantially the same biological function or activity as the mature polypeptide encoded by the DNA of SEQ.ID.NO.:9.

The present invention further relates to polynucleotides that hybridize to the herein above-described sequences. In this regard, the present invention especially relates to polynucleotides that hybridize under stringent conditions to the herein above-described polynucleotides. There are a large numbers of polynucleotide hybridization techniques known in the art including hybridizations coupling DNA to DNA, RNA to RNA and RNA to DNA. All of these methods can incorporate stringent hybridization conditions to facilitate the accurate identification of nucleic acid targeting to a hybridizable probe. As is known in the art, methods vary depending on the substrate used for hybridization and Maniatis et al. supra, as well as a variety of references in the art detail a number of stringent hybridization techniques. In one example, DNA or RNA samples to be probed are immobilized on a suitable substrate such as nitrocellulose, nylon, polyvinylidene difluoride, or the like. A purified probe, preferably with sufficient specific activity (generally greater than about $10^8$ cpm/µg probe), substantially free of contaminating DNA, protein or unincorporated nucleotides is used. Where nitrocellulose is used, and the immobilized nucleic acid is DNA immobilized on nitrocellulose, the nitrocellulose with DNA is incubated with a hybridization solution comprising 50% formamide-deionized, 6×SSC, 1% SDS, 0.1% Tween 20 and 100 µg/ml t RNA at 42° C. for 15 minutes. Probe is added and the nitrocellulose is further immobilized at 42° C. for about 12-19 hours. The nitrocellulose is then washed in at least two successive washes at 22° C. followed by stringent washes at 65° C. in a buffer of 0.04M sodium phosphate, pH 7.2, 1% SDS and 1 mM EDTA. Conditions for increasing the stringency of a variety of nucleotide hybridizations are well known in the art.

As discussed additionally herein regarding polynucleotide assays of the invention, for instance, polynucleotides of the invention may be used as a hybridization probe for RNA, cDNA and genomic DNA to isolate full-length cDNAs and genomic clones encoding the sequences of SEQ.ID.NO.:9 and to isolate cDNA and genomic clones of other genes that have a high sequence similarity to SEQ.ID.NO.:9. Such probes generally will comprise at least 15 bases. Preferably, such probes will have at least 30 bases and may have at least 50 bases. Particularly preferred probes will have at least 30 bases and preferably will have 50 bases or less. For example, the coding region of the gene of the invention may be isolated using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of SEQ.ID.NO.:10 (in particular the mature polypeptide, i.e., without the signal peptide) as well as polypeptides which have at least 70% identity to the polypeptide of SEQ.ID.NO.:10, preferably at least 80% identity to the polypeptide of SEQ.ID.NO.:10, and more preferably at least 90% similarity (more preferably at least 90% identity) to the polypeptide of SEQ.ID.NO.:10 and still more preferably at least 95% similarity (still more preferably at least 97% identity) to the polypeptide of SEQ.ID.NO.:10. Polypeptides of this invention also include polypeptide fragments. Preferred polypeptide fragments generally containing at least 30 amino acids and more preferably at least 50 amino acids. Representative examples of polypeptide fragments of the invention, include, for example, truncated polypeptides of SEQ.ID.NO.:10. Truncated polypeptides include polypeptides having the amino acid sequence of SEQ.ID.NO.:10, or of variants or derivatives thereof and include a deletion of a continuous series of residues (that is, a continuous region, part or portion) that includes the amino terminus or a continuous series of residues that includes the carboxyl terminus or, as in double truncation mutants, deletion of two continuous series of residues, one including the amino terminus and one including the carboxyl terminus.

Polypeptides of this invention also include fragments that have one or more functional characteristics of the mature protein, such as gabapentin binding and the like that are shared by the polypeptides characterized by SEQ.ID.NO.:10. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity, an improved activity, or with a decreased undesirable activity.

Recombinant Expression of a Calcium Channel $\alpha_2\delta$-4 Subunit

The cloned calcium channel $\alpha_2\delta$-4 subunit DNA obtained through the methods described herein may be recombinantly expressed by molecular cloning into an expression vector containing a suitable promoter and other appropriate transcription regulatory elements and transferred into prokaryotic or eukaryotic host cells to produce a recombinant calcium channel $\alpha_2\delta$-4 subunit protein. Techniques for such manipulations are fully described in Maniatis, T, et al, supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including E. coli, bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector preferably contains an origin of replication for autonomous replication in host cells, selectable markers, at least one restriction endonuclease recognition site, a potential for high copy number, and active promoters. A promoter is defined as a DNA sequence that directs a RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant calcium channel $\alpha_2\delta$-4 subunits in mammalian cells. Commercially available mammalian expression vectors which may be suitable for recombinant calcium channel $\alpha_2\delta$-4 subunit expression include, but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express a recombinant calcium channel $\alpha_2\delta$-4 subunit in bacterial cells. Commercially available bacterial expression vectors that may be suitable for recombinant calcium channel $\alpha_2\delta$-4 subunit expression include, but are not limited to, pET vectors (Novagen) and pQE vectors (Qiagen).

A variety of fungal cell expression vectors may be used to express a recombinant $\alpha2\delta$-4 calcium channel subunit in fungal cells such as yeast. Commercially available fungal cell expression vectors suitable for recombinant calcium channel $\alpha_2\delta$-4 subunit expression include, but are not limited, to pYES2 (Invitrogen) and Pichia expression vectors (Invitrogen).

A variety of insect cell expression vectors may be used to express a recombinant calcium channel $\alpha_2\delta$-4 subunit in insect cells. Commercially available insect cell expression vectors suitable for the recombinant expression of a calcium channel $\alpha_2\delta$-4 subunit include, but are not limited to pBlueBacII (Invitrogen).

DNA encoding a calcium channel $\alpha_2\delta$-4 subunit may be cloned into an expression vector for expression in a recombinant host cell. Recombinant host cells may be prokaryotic or eukaryotic, including, but not limited to, bacteria such as E. coli, fungal cells such as yeast, mammalian cells including, but not limited to, cell lines of human, bovine, porcine, monkey and rodent origin, and insect cells including, but not limited to, drosophila and silkworm derived cell lines. Cell lines derived from mammalian species that are commercially available and can be used in this invention include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including, but not limited to, transformation, transfection, protoplast fusion, lipofection, and electroporation. The expression vector-containing cells are clonally propagated and individually analyzed to determine whether they produce calcium channel $\alpha_2\delta$-4 subunit protein. The identification of calcium channel $\alpha_2\delta$-4 subunit expressing host cell clones may be performed using antibody recognizing the calcium channel $\alpha_2\delta$-4 subunit or alternatively, cells expressing the subunit can be identified based on the presence of host cell-associated calcium channel $\alpha_2\delta$-4 subunit activity.

Expression of calcium channel $\alpha_2\delta$-4 subunit DNA may also be performed using in vitro produced synthetic mRNA. Synthetic mRNA or mRNA isolated from calcium channel $\alpha_2\delta$-4 subunit producing cells can be efficiently translated in various cell-free systems including, but not limited to, wheat germ extracts and reticulocyte extracts. mRNA can also be translated in cell based systems by, for example, microinjection into frog oocytes.

To determine the calcium channel $\alpha_2\delta$-4 subunit DNA sequence(s) that yields optimal levels of calcium channel $\alpha_2\delta$-4 subunit activity and/calcium channel $\alpha_2\delta$-4 subunit protein, calcium channel $\alpha_2\delta$-4 subunit DNA molecules can be constructed. One construct contemplated for use is the full-length open reading frame of the calcium channel $\alpha_2\delta$-4 subunit cDNA encoding a protein of 1090 amino acids and corresponding to approximately base 189 to approximately base 3472 of SEQ ID NO.:9 (these numbers correspond to the first nucleotide of the first methionine and last nucleotide before the first stop codon). Other constructs are those that contain portions of the cDNA that encode a calcium channel $\alpha_2\delta$-4 subunit protein. All constructs can be designed to contain none, all or portions of the 5' or the 3' untranslated region of a calcium channel $\alpha_2\delta$-4 subunit cDNA. Calcium channel $\alpha_2$5-4 subunit activity and levels of protein expression can be determined following the introduction, both singly or in combination, of these constructs into appropriate host cells. Once the calcium channel $\alpha_2\delta$-4 subunit DNA cassette yielding optimal expression in transient assays has been identified, this calcium channel $\alpha_2\delta$-4 subunit DNA construct can be transferred to a variety of expression vectors for expression in host cells including, but not limited to, mammalian cells, baculovirus-infected insect cells, E. coli, and the yeast S. cerevisiae.

Assay Methods for the Calcium Channel $\alpha_2\delta$-4 Subunit

Host cell transfectants and microinjected oocytes may be used to assay both the level of functional calcium channel $\alpha_2\delta$-4 subunit activity and the level of total calcium channel $\alpha_2\delta$-4 subunit protein by the following methods. In the case of recombinant host cells, this involves the co-transfection of one or possibly two or more constructs, containing cDNAs encoding the calcium channel $\alpha_2\delta$-4 subunit, and the suitable $\alpha_1$ and $\beta$ subunits. In the case of oocytes, this involves the injection of synthetic RNA for calcium channel $\alpha_2\delta$-4 subunit protein or co-injection of synthetic RNA for calcium channel $\alpha_2\delta$-4 with synthetic RNAs for calcium channel $\alpha_1$ and $\beta$ subunits. Following an appropriate period of time to allow for expression, cellular proteins are metabolically labelled with, for example $^{35}$S-methionine for 24 hours, after which cell lysates and cell culture supernatants are harvested and subjected to immunoprecipitation with polyclonal antibodies directed against the calcium channel $\alpha_2\delta$-4 subunit protein.

Levels of calcium channel $\alpha_2\delta$-4 subunit protein in host cells can be quantitated by immunoaffinity and/or ligand affinity techniques. Cells expressing calcium channel $\alpha_2\delta$-4 subunit can be assayed for the number of calcium channel $\alpha_2\delta$-4 subunit molecules expressed by measuring the amount of radioactive ligand binding to cell membranes. Calcium channel $\alpha_2\delta$-4 channel subunit-specific affinity beads or calcium channel $\alpha_2\delta$-4 subunit-specific antibodies are used to isolate for example $^{35}$S-methionine labelled or unlabelled calcium channel $\alpha_2\delta$-4 subunit protein. Labelled calcium channel $\alpha_2\delta$-4 subunit protein can be isolated, for example, by SDS-PAGE. Unlabelled calcium channel $\alpha_2\delta$-4 subunit protein is detected by Western blotting, ELISA or RIA assays employing calcium channel $\alpha_2\delta$-4 subunit specific antibodies.

Other methods for detecting calcium channel $\alpha_2\delta$-4 subunit activity involve the direct measurement of calcium channel $\alpha_2\delta$-4 subunit activity in whole cells co-transfected with the calcium channel $\alpha_2\delta$-4, $\alpha_1$ and $\beta$ subunit cDNAs or oocytes co-injected with the calcium channel $\alpha_2\delta$-4, or $\alpha_1$ and $\beta$ subunit synthetic RNAs. Calcium channel $\alpha_2\delta$-4 subunit activity is measured by specific ligand binding or by measuring biological characteristics of the host cells expressing calcium channel $\alpha_2\delta$-4 subunit DNA. In the case of recombinant host cells expressing a calcium channel $\alpha_2\delta$-4 subunit, patch voltage clamp techniques can be used to measure channel activity and quantitate calcium channel $\alpha_2\delta$-4 subunit protein. In the case of oocytes, patch clamp as well as two-electrode voltage clamp techniques can be used to measure calcium channel activity and quantitate calcium channel $\alpha_2\delta$-4 subunit protein.

Cell Based Assays

The present invention provides a whole cell method to detect compound modulation of a calcium channel $\alpha_2\delta$-4 subunit. The method comprises the steps of;

1) contacting a compound with a cell containing a functional calcium channel $\alpha_2\delta$-4 subunit, and 2) measuring a change in the cell in response to the contacting step.

The amount of time necessary for cellular contact with the compound is empirically determined, for example, by running a time course with a known calcium channel $\alpha_2\delta$-4 subunit modulator and measuring cellular changes as a function of time.

The term "functional" as used herein refers to the expression of an $\alpha_2$ protein-characteristic activity. For example, but not by way of limitation, a functional $\alpha_2\delta$-4 calcium channel may bind gabapentin (GBP) or may act as a voltage-gated calcium channel when expressed with its calcium channel complex proteins, the alpha2, beta, and gamma subunits.

The measurement means of the method of the present invention can be further defined by comparing a cell that has been exposed to a compound to an identical cell that has not been similarly exposed to the compound. Alternatively two cells, one containing a calcium channel $\alpha_2\delta$-4 subunit and a second cell identical to the first, but lacking a calcium channel $\alpha_2\delta$-4 subunit can both be contacted with the same compound and compared for differences between the two cells. This technique is also useful in establishing the background noise of these assays. One of ordinary skill in the art will appreciate that these control mechanisms also allow easy selection of cellular changes that are responsive to modulation of functional calcium channel $\alpha_2\delta$-4 subunit.

The term "cell" refers to at least one cell, but includes a plurality of cells appropriate for the sensitivity of the detection method. Cells suitable for the present invention may be bacterial, yeast, or eukaryotic.

The assay methods to determine compound modulation of functional calcium channel $\alpha_2\delta$-4 subunit can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage or to minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, greater numbers of samples may be assayed using the design of the present invention.

The cellular changes contemplated within the method of the present invention comprise directly measuring changes in the function or quantity of the $\alpha 2\delta$-4 calcium channel subunit or by measuring downstream effects of $\alpha 2\delta$-4 calcium channel subunit function, for example by measuring secondary messenger concentrations or changes in transcription or by detecting changes in the protein levels of genes that are transcriptionally influenced by the calcium channel $\alpha_2\delta$-4 subunit. Alternatively phenotypic changes can be measured in the cell. Preferred measurement means include changes in the quantity of calcium channel $\alpha_2\delta$-4 subunit protein, changes in the functional activity of the calcium channel $\alpha_2\delta$-4 subunit, changes in the quantity of mRNA, changes in intracellular protein, changes in cell surface protein, or secreted protein, or changes in $Ca^{2+}$, cAMP or GTP concentration. Changes in the quantity or functional activity of calcium channel $\alpha_2\delta$-4 subunit are described herein. Changes in the levels of mRNA are detected by reverse transcription polymerase chain reaction (RT-PCR) or by differential gene expression. Immunoaffinity, ligand affinity, or enzymatic measurement quantitates changes in levels of protein in host cells. Protein-specific affinity beads or specific antibodies can be used to isolate labeled or unlabelled protein. Labelled protein can be visualized after separation by SDS-PAGE. Unlabelled protein can be detected by Western blotting, cell surface detection by fluorescent cell sorting, cell image analysis, ELISA or RIA employing specific antibodies. Where the protein is an enzyme, the induction of protein is monitored by cleavage of a flourogenic or calorimetric substrate.

Alternatively, cells expressing recombinant protein can be used in binding assays to determine if a compound inhibits gabapentin binding to the $\alpha_2\delta$-4 subunit by a method comprising the steps of:
(a) incubating a cell membrane from a cell expressing recombinant $\alpha_2\delta$-4 with radioactive gabapentin (GBP) and a candidate compound, wherein the membrane comprises an $\alpha2\delta$ subunit of calcium channel and where the contact is for sufficient time to allow GBP binding to the $\alpha2\delta$ subunit of calcium channels in the cell membranes,
(b) separating the cell membranes from unbound radioactive GBP,
(c) measuring binding of the radioactive GBP to the cell membranes, and
(d) identifying a compound that inhibits GBP binding by a reduction of the amount of radioactive GBP in step (c) to an established control.

The present invention is also directed to methods for screening for compounds that modulate the expression of DNA or RNA encoding a calcium channel $\alpha_2\delta$-4 subunit as well as screening methods to identify those compounds that modulate the function of a calcium channel $\alpha_2\delta$-4 subunit protein in vivo. Compounds may increase or attenuate DNA or RNA expression or increase or attenuate a particular function of the calcium channel $\alpha_2\delta$-4 subunit protein. Compounds that modulate the expression of DNA or RNA encoding calcium channel $\alpha_2\delta$-4 subunit or the function of calcium channel $\alpha_2\delta$-4 subunit protein may be detected by a variety of assays.

For example, the assay can be a simple "yes/no" assay to determine whether there is a change in expression or function. The assay can be a quantitative assay and compare the expression or function of a test sample with the levels of expression or function in a standard sample. Modulators identified in this process can be tested for their use as therapeutic agents.

Purification of the Calcium Channel $\alpha_2\delta$-4 Subunit Protein

Following expression of a calcium channel $\alpha_2\delta$-4 subunit of this invention in a recombinant host cell, the calcium channel $\alpha_2\delta$-4 subunit protein may be recovered to provide a purified calcium channel $\alpha_2\delta$-4 subunit in active form. Several calcium channel $\alpha_2\delta$-4 subunit purification procedures are available and suitable for use. For example, as discussed above, a recombinant calcium channel $\alpha_2\delta$-4 subunit may be purified from cell lysates and extracts or from conditioned culture medium using various combinations of or individual application of salt fractionation, ion exchange chromatography, size exclusion chromatography, hydroxylapatite adsorption chromatography and hydrophobic interaction chromatography, lectin chromatography, and antibody/ligand affinity chromatography.

Recombinant calcium channel $\alpha_2\delta$-4 subunits can be separated from other cellular proteins using an immunoaffinity column made with monoclonal or polyclonal antibodies monospecific for a full length nascent calcium channel $\alpha_2\delta$-4 subunit, specific for polypeptide fragments of a calcium channel $\alpha_2\delta$-4 subunit or specific for calcium channel $\alpha_2\delta$-4 subunit subunits. Once the affinity resin is prepared and loaded onto a column, the affinity resin is equilibrated in a suitable buffer, for example phosphate buffered saline (pH 7.3). The cell culture supernatants or cell extracts containing the calcium channel $\alpha_2\delta$-4 subunit or subunits of the $\alpha_2\delta$-4 calcium channel are slowly passed through the column. The column is washed with the buffer until the optical density ($A_{280}$) falls to background, next the protein is eluted by changing the buffer condition, such as by lowering the pH using a buffer such as 0.23 M glycine-HCl (pH 2.6). The purified calcium channel $\alpha_2\delta$-4 subunit protein is then dialyzed against a suitable buffer such as phosphate buffered saline.

Protein Based Assay

The present invention provides an in vitro protein assay method to detect compound binding to a calcium channel $\alpha_2\delta$-4 subunit protein. The method comprises the steps of;
1) contacting a compound with a measurably labeled ligand for the calcium channel $\alpha_2\delta$-4 subunit protein, and a calcium channel $\alpha_2\delta$-4 subunit protein, and
2) measuring binding of the compound to the protein observed as a reduction in the amount of labeled ligand binding to the calcium channel $\alpha_2\delta$-4 subunit protein.

Production and Use of Antibodies that Bind to the Calcium Channel $\alpha_2\delta$-4 Subunit Monospecific antibodies to calcium channel $\alpha_2\delta$-4 subunit are purified from mammalian antisera containing antibodies reactive against calcium channel $\alpha_2\delta$-4 subunit or are prepared as monoclonal antibodies reactive with a calcium channel $\alpha_2\delta$-4 subunit using well known techniques such as those originally described by Kohler and Milstein, *Nature* 256: 495-497 (1975). Immunological techniques are well known in the art and described in, for example, *Antibodies: A laboratory manual* published by Cold Spring Harbor Laboratory Press, Cold Spring Harbor, N.Y., ISBN 0879693142.

Monospecific antibody as used herein is defined as a single antibody species or multiple antibody species with homogenous binding characteristics for a calcium channel $\alpha_2\delta$-4 subunit. Homogenous binding as used herein refers to the ability of the antibody species to bind to a specific antigen or epitope, such as those associated with the $\alpha2\delta$-4 calcium channel subunit, as described above. Calcium channel $\alpha_2\delta$-4 subunit monospecific antibodies are raised by immunizing animals such as mice, rats, guinea pigs, rabbits, goats, horses and the like, with rabbits being preferred, with an appropriate concentration of calcium channel $\alpha_2\delta$-4 subunit either with or without an immune adjuvant.

Preimmune serum is collected prior to the first immunization. Each animal receives between about 0.001 mg and about 1000 mg of calcium channel $\alpha_2\delta$-4 subunit associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization can consist of calcium channel $\alpha_2\delta$-4 subunit in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with the calcium channel $\alpha_2\delta$-4 subunit are prepared by immunizing inbred mice, preferably Balb/c, with the calcium channel $\alpha_2\delta$-4 subunit or a fragment thereof. The mice are immunized by the intraperitoneal (IP) or subcutaneous (SC) route with about 0.001 mg to about 1.0 mg, preferably about 0.1 mg, of calcium channel $\alpha_2\delta$-4 subunit in about 0.1 ml buffer or saline incorporated in an equal volume of an acceptable adjuvant, as discussed above. Freund's adjuvant is preferred and in a preferred embodiment, Freund's complete adjuvant is used for the initial immunization with Freund's incomplete adjuvant used thereafter. The mice receive an initial immunization on day 0 and are rested for about 2 to about 30 weeks. Immunized mice are given one or more booster immunizations of about 0.001 to about 1.0 mg of calcium channel $\alpha_2\delta$-4 subunit in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art.

Supernatant fluids are collected from growth positive wells on about days 14, 18, and 21 and are screened for antibody production by an immunoassay such as a solid phase immunoradioassay (SPIRA) using a calcium channel $\alpha_2\delta$-4 subunit as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in *Tissue Culture Methods and Applications*, Kruse and Paterson, Eds., Academic Press, 1973 or by the technique of limited dilution.

Monoclonal antibodies are produced in vivo by injection of pristane primed Balb/c mice, approximately 0.5 ml per mouse, with about $1\times10^6$ to about $6\times10^6$ hybridoma cells at least about 4 days after priming. Ascites fluid is collected at approximately 8-12 days after cell transfer and the monoclonal antibodies are purified by techniques known in the art.

In vitro production of anti-calcium channel $\alpha_2\delta$-4 subunit mAb is carried out by growing the hybridoma in tissue culture media well known in the art. High density in vitro cell culture may be conducted to produce large quantities of anti-calcium channel $\alpha_2\delta$-4 subunit mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of the $\alpha2\delta$-4 calcium channel subunit in body fluids or tissue and cell extracts.

It is readily apparent to those skilled in the art that the above described methods for producing monospecific antibodies may be used to produce antibodies specific for calcium channel $\alpha_2\delta$-4 subunit polypeptide fragments, full-length nascent calcium channel $\alpha_2\delta$-4 subunit polypeptide, or the individual calcium channel $\alpha_2\delta$-4 subunit subunits. Specifically, it is readily apparent to those skilled in the art that monospecific antibodies may be generated which are specific for only one calcium channel $\alpha_2\delta$-4 subunit or the fully functional calcium channel $\alpha_2\delta$-4 subunit protein. It is also apparent to those skilled in the art that monospecific antibodies may be generated that inhibit the normal function of calcium channel $\alpha_2\delta$-4 subunit protein.

Calcium channel $\alpha_2\delta$-4 subunit antibody affinity columns are made by adding the antibodies to a gel support such that the antibodies form covalent linkages with the gel bead support. Preferred covalent linkages are made through amine, aldehyde, or sulfhydryl residues contained on the antibody. Methods to generate aldehydes or free sulfydryl groups on antibodies are well known in the art; amine groups are reactive with, for example, N-hydroxysuccinimide esters.

Kit Compositions Containing Calcium Channel $\alpha_2\delta$-4 Subunit Specific Reagents Kits containing calcium channel $\alpha_2\delta$-4 subunit DNA or RNA, antibodies to calcium channel $\alpha_2\delta$-4 subunit, or calcium channel $\alpha_2\delta$-4 subunit protein may be prepared. Such kits are used to detect DNA which hybridizes to calcium channel $\alpha_2\delta$-4 subunit DNA or to detect the presence of calcium channel $\alpha_2\delta$-4 subunit protein or peptide fragments in a sample. Such characterization is useful for a variety of purposes including, but not limited to, forensic analyses, diagnostic applications, and epidemiological studies.

The DNA molecules, RNA molecules, recombinant protein and antibodies of the present invention may be used to screen and measure levels of calcium channel $\alpha_2\delta$-4 subunit DNA, calcium channel $\alpha_2\delta$-4 subunit RNA or calcium channel $\alpha_2\delta$-4 subunit protein. The recombinant proteins, DNA molecules, RNA molecules and antibodies lend themselves to the formulation of kits suitable for the detection and typing of a calcium channel $\alpha_2\delta$-4 subunit. Such a kit would comprise a compartmentalized carrier suitable to hold in close confinement at least one container. The carrier would further comprise reagents such as recombinant calcium channel $\alpha_2\delta$-4 subunit protein or anti-calcium channel $\alpha_2\delta$-4 subunit antibodies suitable for detecting a calcium channel $\alpha_2\delta$-4 subunit. The carrier may also contain a means for detection such as labeled antigen or enzyme substrates or the like.

Gene Therapy

Nucleotide sequences that are complementary to the calcium channel $\alpha_2\delta$-4 subunit encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other calcium channel $\alpha_2\delta$-4 subunit antisense oligonucleotide mimetics. Calcium channel $\alpha_2\delta$-4 subunit antisense molecules may be introduced into cells by microinjection, liposome encapsulation or by expression from vectors harboring the antisense sequence. Calcium channel $\alpha_2\delta$-4 subunit antisense therapy may be particularly useful for the treatment of diseases where it is beneficial to reduce calcium channel $\alpha_2\delta$-4 subunit activity.

Calcium channel $\alpha_2\delta$-4 subunit gene therapy may be used to introduce a calcium channel $\alpha_2\delta$-4 subunit into the cells of target organisms. The calcium channel $\alpha_2\delta$-4 subunit gene can be ligated into viral vectors that mediate transfer of the calcium channel $\alpha_2\delta$-4 subunit DNA by infection of recipient host cells. Suitable viral vectors include retrovirus, adenovirus, adeno-associated virus, herpes virus, vaccinia virus, polio virus and the like. Alternatively, calcium channel $\alpha_2\delta$-4 subunit DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo calcium channel $\alpha_2\delta$-4 subunit gene therapy. Calcium channel $\alpha_2\delta$-4 subunit gene therapy may be particularly useful for the treatment of diseases where it is beneficial to elevate calcium channel $\alpha_2\delta$-4 subunit activity. Protocols for molecular methodology of gene therapy suitable for use with the calcium channel $\alpha_2\delta$-4 subunit gene is described in *Gene Therapy Protocols*, edited by Paul D. Robbins, Human press, Totowa N.J., 1996.

Pharmaceutical Compositions

Pharmaceutically useful compositions comprising calcium channel $\alpha_2\delta$-4 subunit DNA, calcium channel $\alpha_2\delta$-4 subunit RNA, or calcium channel $\alpha_2\delta$-4 subunit protein, or modulators of calcium channel $\alpha_2\delta$-4 subunit receptor activity may be formulated according to known methods such as by the admixture of a pharmaceutically acceptable carrier. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of calcium channel $\alpha_2\delta$-4 subunit-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the calcium channel $\alpha_2\delta$-4 subunit receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of calcium channel $\alpha_2\delta$-4 subunit can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a calcium channel $\alpha_2\delta$-4 subunit modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the $\alpha_2\delta$-4 calcium channel subunit receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen using the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tr/agacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

All references cited here in are expressly incorporated by reference into this disclosure. The following examples illustrate the present invention without, however, limiting the same thereto.

EXAMPLE 1

Identifying a Novel Human $\alpha_2\delta$ Subunit

The phrase "Calcium Channel" was used as key words to search the Genbank non-redundant DNA database. Twenty-nine hits were identified as related to $\alpha_2\delta$ subunits. Further sequence analysis led to identify two overlapping EST clones that might encode a novel human calcium channel $\alpha_2\delta$ subunit. The accession numbers are AA001473 (572 bp in length) and H86016 (306 bp in length). The two clones were almost 100% identical in the 292 bp overlapping region, suggesting that they might encode the same polypeptide. The BLAXTX search against the Genbank non-redundant protein database revealed that the longer clone AA001473 was 40% identical to the mouse calcium channel $\alpha_2\delta$-3 subunit over residues 839 to 977 (Accession No. AJ10949), 36% identical to human calcium channel $\alpha_2\delta$-2a subunit over residues 870 to 949 (Accession No. AF042793) and 34% identical to the human calcium channel $\alpha_2\delta$-1a subunit from residues 836 to 927 (Accession No. U73483), respectively.

EXAMPLE 2

Cloning of Human Voltage Gated Calcium Channel $\alpha_2\delta$-4 Subunit

Rapid Amplification of cDNA End (RACE-PCR): In order to clone full-length human calcium channel $\alpha_2\delta$-4 subunit, three rounds of RACE-PCR were used. For the first round of RACE-PCR, two primers were synthesized based on the N-terminal sequence of EST clone AA001473. They were A2-4-9 (SEQ.ID.NO.:1 5'-CAG GGG CTG GGC TGC ACT GTG GTG GTG-3') and A2-4-10 (SEQ.ID.NO.:2 5'-CTC TCG GGA CCT CTT GGA GAT CAG AAT-3'). Primary Race PCR was performed in a 50 µl final volume. The reaction mixture contained 5 µl of Marathon-Ready™ human brain cDNA purchased from Clontech (Palo Alto, Calif.), 5 µl of 10× reaction buffer, 200 µM dNTP, 200 nM AP1 primer (Clontech, SEQ.ID.NO.:3 5'-CCA TCC TAA TAC GAC TCA CTA TAG GGC-3'), 200 nM human calcium channel $\alpha_2\delta$-4 subunit specific primer A2-4-9 and 1 µl of 50× Advatage2 DNA polymerase mixture (Clontech). The thermal cycler parameter for RACE-PCR was: initial denaturing at 94° C. for 30 sec, 5 cycles of 94° C./5 sec and 72° C./4 min, 5 cycles of 94° C./5 sec and 70° C./4 min, and 20 cycles of 94° C./5 sec and 68° C./4 min.

Nest PCR After RACE-PCR reaction, the nest PCR was performed directly to further enhance the amplification of human calcium channel α₂δ-4 subunit. The reaction mixture (in 50 μl final volume) contained: 5 μl of the above RACE PCR product, 5 μl of 10× reaction buffer, 200 μM dNTP, 200 nM AP2 primer (Clontech, SEQ.ID.NO.:4 5'-ACT CAC TAT AGG GCT CGA GCG GC-3'), 200 nM human calcium channel α₂δ-4 subunit specific primer A2-4-10 and 1 μl of 50× Advantage2 DNA polymerase mixture (Clontech). The thermal cycler parameters for the nest PCR reaction was: initial denaturing at 94° C. for 30 sec, 5 cycles of 94° C./5 sec and 72° C./4 min, 5 cycles of 94° C./5 sec and 70° C./4 min, and 20 cycles of 94° C./5 sec and 68° C./4 min.

Subcloning The nested PCR product was then subcloned with a TA cloning kit (Invitrogen, CA). Briefly, the nest PCR product was first size fractionated on 1% agarose gel. The DNA fragments that ranged from 1 to 3 kb were excised from the gel and purified with Qiaquick Spin Purification Kit (Qiagen, CA). Six μl of purified nested PCR product was then ligated with 2 μl pCR2.1 (Invitrogen) linearized vector in the presence of 1 μl 10× reaction buffer, and 1 μl of ligase (4 U/μl) at 14° C. for 4 hours. Finally, 2 μl of ligation mixture was used and the product was used to transform bacterial TOP10F' (Invitrogen) competent cells.

Second Round RACE and Nest PCR: Sequencing analysis of the clone NQC45, a product from the first round of 5' end RACE-PCR, revealed that the α₂δ-4 cDNA had been successfully extended about 1.7 kb cDNA toward the 5' end of the cDNA. However, the N-terminal sequence information for the first 320 amino acids was still missing.

In order to clone the cDNA fragment encoding the N-terminal 320 amino acids of the human α₂δ-4 subunit, a second round of RACE-PCR was performed. Based on the N-terminal sequence of NQC45, the human calcium channel α₂δ-4 subunit specific primer A2-4-16 (SEQ.ID.NO.:5 5'-CAG GCT CTG AGC CTG CGA GCT GAG-3') and A2-4-17 (SEQ.ID.NO.:6 5'-ATG TCG TGG TCG TGG TTG ATG ACC AT-3') were synthesized. The second RACE-PCR was performed with A2-4-16 and AP1 primers and followed nested PCR using A2-4-17 and AP2 primers under condition used in the 1$^{st}$ round of RACE and nested PCR. The nested PCR product was then size fractionated on a 1% agarose gel and a DNA fragment about 1 kb was excised, purified and subcloned into a pCR2.1 cloning vector, as described previously.

Sequence analysis of the clones revealed that the second round of RACE-PCR extended the CDNA fragment through to 190 bp of the 5' untranslational region. An in-frame stop codon (TGA) is present 30 bp upstream from the first methionine. The adjacent upstream sequence (CAGGCC ATGG, especially at −3 position G and +4 position G) of the first ATG is similar to a Kozak sequence (5'-GCCA/GCC AUGG-3'), suggesting a site for translational initiation (Kozak, (1991) *J. Cell. Biol.* 115:887-903). Therefore, the translational open reading frame may start at the ATG codon located at position 190. Starting from this ATG codon, the open reading frame contains 3273 bp encoding a polypeptide of 1090 amino acids (SEQ ID NO:10) and having a calculated molecular mass of 123.2 kDa. The deduced primary sequence is shown in SEQ ID NO:9. Protein sequence analysis revealed that the human calcium channel α₂δ-4 subunit containing multiple N-glycosylational sites are located at residues 94, 137, 455, 600, 682 and 1013, respectively. The human α₂δ-4 subunit also contains two putative PKA (protein kinase A) sites (at residues 60 and 633), and 14 PKC sites (protein kinase C).

The primary sequence comparison of the human calcium channel α₂δ-4 subunit with the other human calcium channel α₂δ subunits demonstrated that the human calcium channel α₂δ-4 subunit is 30%, 32% and 61% identical to human calcium channel α₂δ-1, α₂δ-2 and α₂δ-3 subunits, respectively.

Assembly of full-length human calcium channel α₂δ-4 subunit: The full-length human calcium channel α₂δ-4 subunit was assembled and subcloned into pAGA3 vectors as described in Qin et al. (1997), supra, according to standard molecular biology methods. Briefly, the 1.26 kb N-terminal fragment from 190 bp (NcoI site with start codon) to 1452 bp (KpnI which was derived from the pCR2.1 vector) was cloned into the pAGA3 vector. The resulting construct was designated pAGA3/hα₂δ4-NT. The three C-terminal fragments were subcloned into pBS (KS) (Stratagene) by two steps. First, the two 0.9 kb fragments from 1639 bp (HindIII) to 2575 bp (EcoRI) and 2575 (EcoRI) to the end (BglII, derived from vector) were subcloned together with pBS digested with HindIII and BamHI. Then, a 0.3 kb fragment from 1350 bp (SalI, derived from vector) to 1639 bp (HindIII) was subcloned into the construct obtained from the first step following XhoI and HindIII digestion and ligation producing the construct pBS/hα₂δ4-CT. Finally, the 2.1 kb DNA fragment excised from pBS/hα₂δ4-CT by digestion with BglII and XbaI was subcloned into pAGA3/hα₂δ4-NT digested with the same restriction enzymes to generate the full-length human calcium channel α₂δ-4 subunit, pAGA3/hα₂δ-4. The final construct was confirmed by DNA sequencing.

The deduced amino acid sequence (SEQ ID NO.:9) along with the nucleic acid sequence (SEQ ID NO.:10) encoding the human calcium channel α₂δ-4 subunit is provided below:

```
CAGGTACATTCAGCAGAGCCCAAGTCTGCCACTCTCCAACCaGAGGCCCTGGAAGCTTGG      60

GGTCAAGCTCAGTCCTGGGCTCGTCAGCCCGGCCCCACAACCCTCAGCAGGAGaACCTGC     120

CGAGGACATTCAGCACACAGCAGTGCAGCCGCTGGGTCCTGAGGGTTCTCCGCGTCTCCT     180

GCCCAGGCCATGGCTGTAGCTTTAGGGACAAGGAGGAGGGACAGAGTGAAGCTATGGGCT     240
           MetAlaValAlaLeuGlyThrArgArgArgAspArgValLysLeuTrpAla       —

GACACCTTCGGCGGGGACCTGTATAACAcTGTGACCAAATACTCAGGCTCTCTCTTGCTG     300
AspThrPheGlyGlyAspLeuTyrAsnThrValThrLysTyrSerGlySerLeuLeuLeu       —

CAgAAGAAGTACAAGGATGTGGAGTCCAGTCTGAAGATCGAGGAGGTGGATGGCTTGGAG     360
GlnLysLysTyrLysAspValGluSerSerLeuLysIleGluGluValAspGlyLeuGlu       —

CTGGTGAGGAAGTTCTCAGAGGACATGGAGAACATGCTGCGGAGGAAAGTCgAGGCGGTC     420
LeuValArgLysPheSerGluAspMetGluAsnMetLeuArgArgLysValGluAlaVal       —
```

-continued

```
CAgAATCTGGTGGAAGCTGCCGAGGAGGCCGACCTGAACCACGAATTCAATGAATCCCTG    480
GlnAsnLeuValGluAlaAlaGluGluAlaAspLeuAsnHisGluPheAsnGluSerLeu     -

GTGTTCGACTATTACAACTCGGTCCTGATCAACGaGAGGGACGAGAAGGGCaACTTcGTG    540
ValPheAspTyrTyrAsnSerValLeuIleAsnGluArgAspGluLysGlyAsnPheVal     -

GAGCTGGGCGCCGAGTTCCTCCTGGAGTCCAATGCTCaCTTCAGCAACCTGCCGGtGAAC    600
GluLeuGlyAlaGluPheLeuLeuGluSerAsnAlaHisPheSerAsnLeuProValAsn    -

ACCTcCATCAGCAGCGTGCAGCTGCCCACCAACGTGTACAACAAAGACCCAGATATTTTA    660
ThrSerIleSerSerValGlnLeuProThrAsnValTyrAsnLysAspProAspIleLeu    -

AATGGAGTCTACATGTCTGAAgCCTTGAATGCTGTCTTCGTGGAGAACTTCCAGAGAGAC    720
AsnGlyValTyrMetSerGluAlaLeuAsnAlaValPheValGluAsnPheGlnArgAsp    -

CCAACGTTGACCTGGCAATATTTTGGCAGTGCAACTGGATTCTTCAGGAtCTATCCAGGT    780
ProThrLeuThrTrpGlnTyrPheGlySerAlaThrGlyPhePheArgIleTyrProGly    -

ATAAAATGGACACCTGaTGAGAATGGAGTCATTACTTTTGACTGCCGAAACCGCGGCTGG    840
IleLysTrpThrProAspGluAsnGlyValIleThrPheAspCysArgAsnArgGlyTrp    -

TACATTCAAGCTGCTACTTCTCCCAAGGACATAGTGATTTTGGTGGACGTGAGCGGCAGT    900
TyrIleGlnAlaAlaThrSerProLysAspIleValIleLeuValAspValSerGlySer    -

ATGAAGGGGCTGAGGATGACTATTGCCaAGCACaCCATCACCACCATCTTGGACACCCTG    960
MetLysGlyLeuArgMetThrIleAlaLysHisThrIleThrThrIleLeuAspThrLeu    -

GGGGAGAATGACtTCGTTAATATCATAGCGTACAATGACTACGTCCATTACATCGAGCCT    1020
GlyGluAsnAspPheValAsnIleIleAlaTyrAsnAspTyrValHisTyrIleGluPro    -

TGTTTTAAAGGGATCCTCGTCCaGGCGGACCGAGACAATCGAGAGCATTTCAAACTgCTG    1080
CysPheLysGlyIleLeuValGlnAlaAspArgAspAsnArgGluHisPheLysLeuLeu

GTGGAGGAGTTGATGGTCAAAgGTGTGGGGGTCGTGGACCAAGCCCTGAGAGAAGCCTTC    1140
ValGluGluLeuMetValLysGlyValGlyValValAspGlnAlaLeuArgGluAlaPhe

CAGATCCTGAAgCAGTTCCAAGAgGCCAAGCAAGGAAGCCTCTGCAACCAGGCCATCATG    1200
GlnIleLeuLysGlnPheGlnGluAlaLysGlnGlySerLeuCysAsnGlnAlaIleMet

CTCATCAgCGACgGCGCCGTGGAGGACTACGAGCCGGTGTTTGAGAAGTATAACTGGCCA    1260
LeuIleSerAspGlyAlaValGluAspTyrGluProValPheGluLysTyrAsnTrpPro

GACTGTAAGGTCCGAGTTTTCACTTACCTCATTGGGAGAGAAGTGTCTTTTGCTGACCGC    1320
AspCysLysValArgValPheThrTyrLeuIleGlyArgGluValSerPheAlaAspArg

ATGAAGTGGATTGCATGCAACAACAAAGGctACTACACGCAGATCTCAACGCTGGCGGAC    1380
MetLysTrpIleAlaCysAsnAsnLysGlyTyrTyrThrGlnIleSerThrLeuAlaAsp

ACCCAGGAGAACGTGATGGAATACCTGCACGTGCTCAGCCGCCCCATGGTCATCAACCAC    1440
ThrGlnGluAsnValMetGluTyrLeuHisValLeuSerArgProMetValIleAsnHis

GACCACGACATCATCTGGACAGAGGCCTACATGGACAGCAAGCTCCTCAGCTCGCAGGCT    1500
AspHisAspIleIleTrpThrGluAlaTyrMetAspSerLysLeuLeuSerSerGlnAla

CAGAGCCTGACACTGCTCACCACTGTGGCCATGCCAGTCTTCAGCAAGAAGAACGAAACG    1560
GlnSerLeuThrLeuLeuThrThrValAlaMetProValPheSerLysLysAsnGluThr

CGATCCCATGGCATTCTCCTGGGTGTGGTGGGCTCAGATGTGGCCCTGAGAGAGCTGATG    1620
ArgSerHisGlyIleLeuLeuGlyValValGlySerAspValAlaLeuArgGluLeuMet

AAGCTGGCGCCCCGGTACAAGCTTGGAGTGCACGGATACGCCTTTCTGAACACCAACAAT    1680
LysLeuAlaProArgTyrLysLeuGlyValHisGlyTyrAlaPheLeuAsnThrAsnAsn

GGCTACATCCTCTCCCATCCCGACCTCCGGCCCCTGTACAGAGAGGGGAAGAAACTAAAA    1740
GlyTyrIleLeuSerHisProAspLeuArgProLeuTyrArgGluGlyLysLysLeuLys

CCCAAACCTAACTACAACAGTGTGGATCTCTCCGAAGTGGAGTGGGAAGACCAGGCTGAA    1800
ProLysProAsnTyrAsnSerValAspLeuSerGluValGluTrpGluAspGlnAlaGlu

TCTCTGAGAACAGCCATGATCAATAGGGAAACAGGTACTCTCTCGATGGATGTGAAGGTT    1860
SerLeuArgThrAlaMetIleAsnArgGluThrGlyThrLeuSerMetAspValLysVal

CCGATGGATAAAGGGAAGCGAGTTCTTTTCCTGACCAATGACTACTTCTTCACGGACATC    1920
ProMetAspLysGlyLysArgValLeuPheLeuThrAsnAspTyrPhePheThrAspIle

AGCGACACCCCTTTCAGTTTGGGGGCGGTGCTGTCCCGGGGCCACGGAGAATACATCCTT    1980
SerAspThrProPheSerLeuGlyAlaValLeuSerArgGlyHisGlyGluTyrIleLeu

CTGGGGAACACGTCTGTGGAAGAAGGCCTGCATGACTTGCTTCACCCAGACCTGGCCCTG    2040
LeuGlyAsnThrSerValGluGluGlyLeuHisAspLeuLeuHisProAspLeuAlaLeu
```

```
GCCGGTGACTGGATCTACTGCATCACAGATATTGACCCAGACCACCGGAAGCTCAGCCAG      2100
AlaGlyAspTrpIleTyrCysIleThrAspIleAspProAspHisArgLysLeuSerGln

CTAGAGGCCATGATCCGCTTCCTCACCAGGAAGGACCCAGACCTGGAGTGTGACGAGGAG      2160
LeuGluAlaMetIleArgPheLeuThrArgLysAspProAspLeuGluCysAspGluGlu

CTGGTCCGGGAGGTGCTGTTTGACGCGGTGGTGACAGCCCCCATGGAAGCCTACTGGACA      2220
LeuValArgGluValLeuPheAspAlaValValThrAlaProMetGluAlaTyrTrpThr

GCGCTGGCCCTCAACATGTCCGAGGAGTCTGAACACGTGGTGGACATGGCCTTCCTGGGC      2280
AlaLeuAlaLeuAsnMetSerGluGluSerGluHisValValAspMetAlaPheLeuGly

ACCCGGGCTGGCCTCCTGAGAAGCAGCTTGTTCGTGGGCTCCGAGAAGGTCTCCGACAGG      2340
ThrArgAlaGlyLeuLeuArgSerSerLeuPheValGlySerGluLysValSerAspArg

AAGTTCCTGACACCTGAGGACGAGGCCAGCGTGTTCACCCTGGACCGCTTCCCGCTGTGG      2400
LysPheLeuThrProGluAspGluAlaSerValPheThrLeuAspArgPheProLeuTrp

TACCGCCAGGCCTCAGAGCATCCTGCTGGCAGCTTCGTCTTCAACCTCCGCTGGGCAGAA      2460
TyrArgGlnAlaSerGluHisProAlaGlySerPheValPheAsnLeuArgTrpAlaGlu

GGACCAGAAAGTGCGGGTGAACCCATGGTGGTGACGGCAAGCACAGCTGTGGCGGTGACC      2520
GlyProGluSerAlaGlyGluProMetValValThrAlaSerThrAlaValAlaValThr

GTGGACAAGAGGACAGCCATTGCTGCAGCCGCGGGCGTCCAAATGAAGCTGGAATTCCTC      2580
ValAspLysArgThrAlaIleAlaAlaAlaAlaGlyValGlnMetLysLeuGluPheLeu

CAGCGCAAATTCTGGGCGGCAACGCGGCAGTGCAGCACTGTGGATGGGCCGTACACACAG      2640
GlnArgLysPheTrpAlaAlaThrArgGlnCysSerThrValAspGlyProTyrThrGln

AGCTGCGAGGACAGTGATCTGGACTGCTTCGTCATCGACAACAACGGGTTCATTCTGATC      2700
SerCysGluAspSerAspLeuAspCysPheValIleAspAsnAsnGlyPheIleLeuIle

TCCAAGAGGTCCCGAGAGACGGGAAGATTTCTGGGGGAGGTggaTGGTGCTGTCCTGACC      2760
SerLysArgSerArgGluThrGlyArgPheLeuGlyGluValAspGlyAlaValLeuThr CAGCTGCTCAGCATGGGGGTGTTCAGCCAAGTGACTATGTATGACTATCAGGCCATGTGC      2820
GlnLeuLeuSerMetGlyValPheSerGlnValThrMetTyrAspTyrGlnAlaMetCys AAACCCTCGAGTCACCACCACAGTGCAGCCCAGCCCCTGGTCAGCCCAATTTCTGCCTTC      2880
LysProSerSerHisHisHisSerAlaAlaGlnProLeuValSerProIleSerAlaPhe TTGACGGCGACCAGGTGGCTGCTGCAGGAGCTGGTGCTGTTCCTGCTGGAGTGGAGTGTC      2940
LeuThrAlaThrArgTrpLeuLeuGlnGluLeuValLeuPheLeuLeuGluTrpSerVal TGGGGCTCCTGGTACGACAGAGGGGCcgaGGCCAAAAGTGTCTTCCATCACTCCCACAAA      3000
TrpGlySerTrpTyrAspArgGlyAlaGluAlaLysSerValPheHisHisSerHisLys CACAagaagCAGGACCCGCTGCagcCCTGcgacaCCgagtACCccgTGTtcGTGTAccaG      3060
HisLysLysGlnAspProLeuGlnProCysAspThrGluTyrProValPheValTyrGln CCGGccaTCCGGGaggCCAACGGGATCGTGGAGTGCGGGCCCTGCCAGAAGGTATTTGTG      3120
ProAlaIleArgGluAlaAsnGlyIleValGluCysGlyProCysGlnLysValPheVal GTGCAGCAGATTCCCAACAGTAACCTCCTCCTCCTGGTGACAGACCCCACCTGTGACTGC      3180
ProAlaIleArgGluAlaAsnGlyIleValGluCysGlyProCysGlnLysValPheVal AGCATCTTCCCACCAGTGCTGCAGGAGGCGACAGAAGTCAAATATAATGCCTCTGTCAAA      3240
SerIlePheProProValLeuGlnGluAlaThrGluValLysTyrAsnAlaSerValLys TGTGACCGGATGCGCTCCCAGaagctccGCCGGCGACCAGACTCCTGCCACGCCTTCCAT      3300
CysAspArgMetArgSerGlnLysLeuArgArgArgProAspSerCysHisAlaPheHis CCAGAGGTGCGGGTTGAGGCGGATCGAGGGTGGGCTGGATTTTCATCCCCAAACCCTCTG      3360
ProGluValArgValGluAlaAspArgGlyTrpAlaGlyPheSerSerProAsnProLeu TGCCTGGGTCTGTGCCCCTGCAGACAGGAGCATATAGGGATGCCAATGAACACACCTGTG      3420
CysLeuGlyLeuCysProCysArgGlnGluHisIleGlyMetProMetAsnThrProVal CCTGTGCTTCTCGGGGGAAACATTCGCGTTTATGCCCTGTGACACTGTGATATAATAAGA      3480
ProValLeuLeuGlyGlyAsnIleArgValTyrAlaLeuEnd

AACAGA                                                            3486
```

EXAMPLE 3

Genomic Structure and Splicing Variants of Human Calcium Channel $\alpha_2\delta$-4 Subunit:

The full-length cDNA sequence of the human calcium channel $\alpha_2\delta$-4 subunit was used to search the Genbank human genome database. The search indicated that the gene encoding the human $\alpha_2\delta$-4 subunit is localized at chromosome 12p13.3, about 400 kb away from the locus of human L-type calcium channel $\alpha_1$ 1.2 ($\alpha_{1C}$) subunit (Ertel, et al., (2000) Neuron 25:533-535). As shown in FIG. 6, the gene encoding the human calcium channel $\alpha_2\delta$-4 subunit is localized at chromosome 12p13.3 and is composed of 36 invariant exons (exon2-exon36) and 4 alternative exons (exon1, 1A, 37 and 37B) spanning about 130 kb of human genome. Both exon1 and 1A have an in-frame start codon and both exon 37 and 37B have an in-frame stop codon indicating that there are four possible types of alternative splicing variants. The human calcium channel $\alpha_2\delta$-4 subunit is encoded by exon1 and exon 37 with 36 invariant exons, while human $\alpha_2\delta$-D is encoded with alternative exon 1A and exon 37B. Another two putative splicing variants are $\alpha_2\delta$-4c (exons 1-36 and exon 37B) and $\alpha_2\delta$-4d (exon 1B and exons 2-37).

The nucleotide and amino acid sequences of exon 1B (The nucleotide sequence is SEQ ID No.: 11 and the amino acid sequence is SEQ ID No.:12) and exon 37B (The nucleotide sequence is SEQ ID No.: 13 and the amino acid sequence is SEQ ID No.:14) are provided below:

```
Exon1B

KOZAK
gccaccATGCCTGCAACTCCCAACTTCCTCGCAAACCCCAGCTCCAGCAG
       M  P  A  T  P  N  F  L  A  N  P  S  S  S  S CCGCTGGATTCCCCTCCAGCCAATGCCCGTGGCCTGGGCCTTTGTGCAGA
 R  W  I  P  L  Q  P  M  P  V  A  W  A  F  V  Q  K AGACCTCGGCCCTCCTGTGGCTGCTGCTTCTAGGCACCTCCCTGTCCCCT
 T  S  A  L  L  W  L  L  L  L  G  T  S  L  S  P

GCGTGGGGACAGGCCAAGATTCCTCTGGAAAC
 A  W  G  Q  A  K  I  P  L  E

Exon 37B

GAGAATGCCCAGGACTGCGGCGGCGCCTCGGACACCTCAGCCTCGCCGCC
 E  N  A  Q  D  C  G  G  A  S  D  T  S  A  S  P  P

CCTACTCCTGCTGCCTGTGTGCCTGGGGGCTACTGCCCCAACTCCTGC
 L  L  L  L  P  V  C  A  W  G  L  L  P  Q  L  L  R

GGTGA
 *
```

EXAMPLE 4

Generation of Polyclonal Anitbodies:

Two peptide sequences derived from both amino and carboxyl termini of the human calcium channel $\alpha_2\delta$-4 subunit were selected in order to raise polyclonal antibodies in rabbits. The amino acid sequences were:

```
(1) Ac-KVSDRKFLTPEDEASVC-amide     (SEQ ID NO.:7)

and (2) Ac-RVEADRGWAGFSSPNPLC-amide.   (SEQ ID NO.:8)
```

The peptides were synthesized and antibodies were raised and purified by BioSource International, Inc. The resulting antibodies were tested by ELISA against the antigen peptides and affinity purified with the same peptides. Serum and affinity purified antibodies were used for immunoanalysis, including as Western blot, immunoprecipitation, immunocytochemistry and immunohistochemistry.

EXAMPLE 5

In Vitro Translation Analysis of Human Calcium Channel $\alpha_2\delta$-4 Subunit.

The full-length cDNA of human calcium channel $\alpha_2\delta$-4 subunit was first subcloned into a pAGA3 vector, which was engineered for high efficiency of in vitro transcription and translation as described in Qin et al. (1997), supra. The subcloning procedure used was described in Example 2 and produced the full-length human calcium channel $\alpha_2\delta$-4 subunit. In vitro translation of the human calcium channel $\alpha_2\delta$-4 subunit was done with TnT® T7 Quick Coupled Transcription/Translation System (Promega) following the vendor recommended protocol. Briefly, 1 µg h$\alpha_2\delta$-4/pAGA3 construct was added to 40 µl of TNT Quick Master Mix with 2 µl of [$^{35}$S]methionine (1000 Ci/mmmol at 10 mCi/ml) in a final volume of 50 µl. The reaction mixture was incubated at 30° C. for 90 min. Two µl of reaction mixture was mixed with an equal volume of SDS/PAGE loading buffer and subjected to 8-16% SDS/PAGE analysis. After electrophoresis, the gel was stained with Commassie Blue R250, dried and exposed to X-ray film. The in vitro translated human calcium channel $\alpha_2\delta$-4 subunit migrated to the molecular weight of 123 kDa as predicted by translation of the amino acid sequences from the corresponding nucleic acid sequences.

The in vitro translated human calcium channel $\alpha_2\delta$-4 subunit was also analyzed by Western blot. Briefly, 1 ml of in vitro translated human calcium channel $\alpha_2\delta$-4 subunit was subjected to 8-16% SDS PAGE. The protein on the gel was then transferred to nitrocellulose. The blot was blocked with 5% dry milk in TTBS (0.5% Tween 20, 100 mM Tris-HCl, pH7.5, 0.9% NaCl) at room temperature for 1 hour and then incubated with affinity purified anti-human $\alpha_2\delta$-4 polyclonal antibodies (1:1000 dilution with fresh block solution) at 4° C. overnight. The next day the blot was washed three times with 100 ml TTBS, and incubated with goat anti-rabbit IgG antibody conjugated with Horseradish Peroxidase (Pierce) at room temperature for 1 hour. After washed three times with 100 ml TTBS, the blot was visualized with luminescent reagents, ECL-Plus (Amersham-Pharmacia Biotech).

EXAMPLE 6

Northern Blot Analysis of the Human Calcium Channel $\alpha_2\delta$-4 Subunit Expression:

Northern blot analysis was used to assess tissue distribution of the human calcium channel $\alpha_2\delta$-4 subunit. The cDNA fragment encoding residues 1-90 of human calcium channel $\alpha_2\delta$-4 subunit was used as probe. To make the probe, a 270 bp DNA fragment was isolated and purified from pAGA3/h$\alpha_2\delta$4-NT by digesting with NcoI and EcoRI. To label the probe, 25 ng of a DNA fragment encoding 1-90 residues of the human calcium channel $\alpha_2\delta$-4 subunit was denatured in final volume of 45 µl at 99° C. for 4 min. The denatured DNA probe was incubated with 5 µl of [$\alpha$ $^{32}$P]dCTP at 6000 Ci/mmol (Amersham Pharmacia Biotech) and then transferred to the tube containing a READY-TO-GO DNA Labelling Bead (-dCTP) (Amersham Pharmacia Biotech) and incubated at 37° C. for 30 min. The labeled probe was then separated from free [α $^{32}$P]dCTP with MICROSPIN G-50 column (Amersham Pharmacia Biotech). The labeled probe was denatured by incubating at 99° C. for 4 min and immediately placed on ice before being added to the hybridization solution.

Human MTN (Multiple Tissue Northern) blot (Cal. No.7760-1) was purchased from Clontech (Palo Alto, Calif.) and included samples from heart, brain, placenta, lung, liver, skeletal muscle, kidney, and pancreas. The blots were prehybridized with 5 ml ExpressHyb Solution (Clontech) at 65° C. for 4 hours, and then hybridized in the presence of $2 \times 10^6$ cpm/μl probe of the human α2δ-4 subunit at 65° C. for overnight. The probe was a [$^{32}$P]-labeled 270 bp cDNA fragment encoding 90 amino terminal residues of the human calcium channel $\alpha_2\delta$-4 subunit. The blots were washed twice with 200 ml of 0.2×SSC/0.1% SDS solution at 65° C. for two hours. Finally the blots were exposed to X-ray film in a −80° C. freezer for 1-3 days.

A 2.0 kb cDNA fragment encoding human β-actin was used as a control probe (FIG. 7B). The same blots were striped with 0.5% SDS at 90° C. for 10 min after hybridization with the human calcium channel $\alpha_2\delta$-4 probe. The blots were then prehybridized with 5 ml of ExpressHyb at 68° C. for 1 hour and then hybridized in the presence of a human β-actin probe for 2 hours at 68° C. The blots were washed twice with 200 ml of 0.2×SSC/0.1% SDS solution at 68° C. for two hours. Finally the blots were exposed to X-ray film in −80° C. freezer for 6 hours. In these studies, the VGCC containing $\alpha_2\delta$-4 appeared most strongly in heart and skeletal muscle.

EXAMPLE 7

Cloning of Human Calcium Channel $\alpha_2\delta$-4 Subunit cDNA into a Mammalian Expression Vector The human calcium channel $\alpha_2\delta$-4 subunit gene was inserted into pcDNA3.1 (Invitrogen) by a three piece ligation. The 850 bp cDNA fragment encoding the amino terminal portion of the human calcium channel $\alpha_2\delta$-4 subunit was obtained from pAGA3/hα$_2$δ-4-NT by digesting with NcoI, followed by blunt end digestion with BamHI. The 2.6 kb cDNA fragment encoding the carboxyl terminal portion of the human calcium channel $\alpha_2\delta$-4 subunit was isolated and purified from pAGA3/hα$_2$δ-4 by digestion with BamHI and XbaI. The two cDNA fragments were ligated together with the vector pcDNA3, previously digested with EcoRV and XbaI. The recombinant plasmids containing the human calcium channel $\alpha_2\delta$-4 subunit were isolated and confirmed by restriction enzyme digestion and DNA sequencing.

The clone pcDNA3.1/hα$_2$δ-4 was used for transient and stable transfection of HEK293 cells by SuperFect (Qiagen) following the vendor's protocol. Stable cell clones were selected for growth in the presence of G418. Single G418 resistant clones were isolated and shown to contain the intact human calcium channel $\alpha_2\delta$-4 subunit cDNA. Clones containing the human calcium channel $\alpha_2\delta$-4 subunit cDNAs were analyzed for expression using immunological techniques, such as Western blot, immunoprecipitation, and immunofluorescence using antibodies specific to the human calcium channel $\alpha_2\delta$-4 subunit. The binding affinity of the human calcium channel $\alpha_2\delta$-4 subunit to Gabapentin was determined by radioactive ligand binding assay.

Cells that were expressing the human calcium channel $\alpha_2\delta$-4 subunit, stably or transiently, were used to test for channel protein expression and for ligand binding activity. These cells were used to identify and examine other compounds for their ability to modulate, inhibit or activate the channel and to compete for radioactive ligand binding.

Cassettes containing the human calcium channel $\alpha_2\delta$-4 subunit cDNA in the positive orientation, with respect to the promoter, were ligated into appropriate restriction sites 3' of the promoter and identified by restriction site mapping and/or sequencing. These cDNA expression vectors were introduced into fibroblast host cells such as COS-7 (ATCC# CRL1651), and CV-1 tat (Sackevitz et al., *Science* 238: 1575 (1987), or 293, L (ATCC#CRL6362) by standard methods including, but not limited to, electroporation, or chemical procedures (such as cationic liposomes, DEAE dextran, or calcium phosphate). Transfected cells and cell culture supernatants were harvested and analyzed for human calcium channel $\alpha_2\delta$-4 subunit expression as described herein.

The vectors used for mammalian transient expression are be used to establish stable cell lines expressing the human calcium channel $\alpha_2\delta$-4 subunit. The human calcium channel $\alpha_2\delta$-4 subunit is expressed extracellularly as a secreted protein by ligating human calcium channel $\alpha_2\delta$-4 subunit cDNA constructs to DNA encoding the signal sequence of a secreted protein, as known in the art. The transfection host cells include, but are not limited to, CV-1-P (Sackevitz et al., *Science* 238: 1575 (1987), tk-L (Wigler, et al. *Cell* 11: 223 (1977), NS/0, and dHFr-CHO (Kaufman and Sharp, *J. Mol. Biol.* 159: 601, (1982).

Co-transfection of any vector containing human calcium channel $\alpha_2\delta$-4 subunit cDNA with a drug selection plasmid including, but not limited to, G418, aminoglycoside phosphotransferase; hygromycin, hygromycin-B phospholransferase; APRT, or xanthine-guanine phosphoribosyl-transferase will allow for the selection of stably transfected clones. Levels of Human α2δ-4 calcium channel subunit are quantitated by the assays described herein.

Human calcium channel $\alpha_2\delta$-4 subunit cDNA constructs are also ligated into vectors containing amplifiable drug-resistance markers for the production of mammalian cell clones synthesizing the highest possible levels of human calcium channel $\alpha_2\delta$-4 subunit. Following introduction of these constructs into cells, clones containing the plasmid are selected with the appropriate agent. Isolation of an over-expressing clone with a high copy number of plasmids, is accomplished by selection in increasing doses of the agent.

The expression of recombinant human calcium channel $\alpha_2\delta$-4 subunit is achieved by transfection of full-length human calcium channel $\alpha_2\delta$-4 subunit cDNA into a mammalian host cell.

EXAMPLE 8

Cloning of Human Calcium Channel $\alpha_2\delta$-4 Subunit cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing Human $\alpha_2\delta$-4 subunit cDNA is produced by the following standard methods (InVitrogen Maxbac Manual): the Human calcium channel $\alpha_2\delta$-4 subunit cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., *Nucl. Acid. Res.* 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, human calcium channel $\alpha_2\delta$-4 subunit expression is measured by the assays described herein.

The cDNA encoding the entire open reading frame for human calcium channel $\alpha_2\delta$-4 subunit is inserted into pBlueBacII. Constructs in the positive orientation are identified by sequence analysis and used to transfect Sf9 cells in the presence of linear AcNPV mild type DNA.

Authentic, active human calcium channel $\alpha_2\delta$-4 subunit is found in the cytoplasm membrane of infected cells. Active human calcium channel $\alpha_2\delta$-4 subunit is extracted from infected cells by methods known in the art (including, for example, hypotonic or detergent lysis).

EXAMPLE 9

Cloning of Human Calcium Channel $\alpha_2\delta$-4 Subunit cDNA into a Yeast Expression Vector Recombinant human calcium channel $\alpha_2\delta$-4 subunit is produced in the yeast *S. cerevisiae* following the insertion of the optimal human calcium channel $\alpha_2\delta$-4 subunit CDNA cistron into expression vectors designed to direct the intracellular or extracellular expression of heterologous proteins. In the case of intracellular expression, vectors such as EmBLyex4, or the like, are ligated to the human calcium channel $\alpha_2\delta$-4 subunit cistron (see Rinas, U. et al., *Biotechnology* 8: 543-545 (1990); and Horowitz B. et al., *J. Biol. Chem.* 265: 4189-4192 (1989). For extracellular expression, the human calcium channel $\alpha_2\delta$-4 subunit cistron is ligated into yeast expression vectors which fuse a secretion signal (a yeast or mammalian peptide) to the $NH_2$ terminus of the Human calcium channel $\alpha_2\delta$-4 subunit protein (Jacobson, M. A., *Gene* 85: 511-516 (1989) and Riett L. and Bellon N. *Biochem.* 28: 2941-2949 (1989).

These vectors include, but are not limited to, pAVE1.6, which fuses the human serum albumin signal to the expressed cDNA (Steep O. *Biotechnology* 8: 42-46 (1990), and the vector pL8PL which fuses the human lysozyme signal to the expressed cDNA (Yamamoto, Y., *Biochem.* 28: 2728-2732). In addition, the human calcium channel $\alpha_2\delta$-4 subunit is expressed in yeast as a fusion protein conjugated to ubiquitin using the vector pVEP (see Ecker, D. J., *J. Biol. Chem.* 264: 7715-7719 (1989), Sabin, E. A., *Biotechnology* 7: 705-709 (1989), and McDonnell D. P., *Mol. Cell Biol.* 9: 5517-5523 (1989). The levels of expressed human calcium channel $\alpha_2\delta$-4 subunit are determined by the assays described herein.

EXAMPLE 10

Purification of Recombinant Human Calcium Channel $\alpha_2\delta$-4 Subunit

Recombinantly produced human calcium channel $\alpha_2\delta$-4 subunit may be purified by antibody affinity chromatography.

Human calcium channel $\alpha_2\delta$-4 subunit antibody affinity columns are made by adding the anti-human calcium channel $\alpha_2\delta$-4 subunit antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents. The cell culture supernatants or cell extracts containing solubilized human calcium channel $\alpha_2\delta$-4 subunit are slowly passed through the column. The column is then washed with phosphate-buffered saline together with detergents until the optical density ($A_{280}$) falls to background, then the protein is eluted with 0.23 M glycine-HCl (pH 2.6) together with detergents. The purified human calcium channel $\alpha_2\delta$-4 subunit protein is then dialyzed against phosphate buffered saline.

EXAMPLE 11

Immunohistochemistry.

Commercial human checkerboard tissue slides (Dako, Carpenteria, Calif.; Biomeda, Foster City, Calif.; Novagen, Milwaukee, Wis.) were deparaffinized, hydrated and processed for routine immunohistochemistry (IHC) as previously described (D'Andrea et al., (1998) *J. Histochem. Cytochem.* 46(1): 1-8. Briefly, slides were microwaved in Target buffer (Dako), cooled, placed in distilled $H_2O$ and then treated with 3.0% $H_2O_2$ for 10 min. Afterwards, the slides were rinsed in phosphate-buffered saline (pH 7.4, PBS) and then processed through an avidin-biotin blocking system according to the manufacturer's instructions (Vector Labs, Burlingame, Calif.) and then placed in PBS. All subsequent reagent incubations and washes were performed at room temperature. Normal blocking serum (Vector Labs) was placed on all slides for 10 min. After briefly rinsing in PBS, primary antibody (affinity purified anti-human $\alpha_2\delta$-4 polyclonal antibodies, 1:1000 dilution) was placed on slides for 30 min. The slides were washed and biotinylated secondary antibody, here goat anti-rabbit (polyclonal antibodies) or horse anti-mouse (monoclonal antibodies) were placed on the tissue sections for 30 min (Vector Labs). After rinsing in PBS, the avidin-horseradish peroxidase-biotin complex reagent (HRP-ABC, Vector Labs) was added for 30 min. Slides were washed and treated with the chromogen 3,3'-diaminobenzidine (DAB, Biomeda) twice for five min each, then rinsed in $dH_2O$, and counterstained with hematoxylin. A monoclonal antibody to vimentin, the widely conserved ubiquitous, intracellular filament protein, was utilized as a positive control to demonstrate tissue antigenicity and control reagent quality. The negative controls included replacement of the primary antibody with pre-immune serum or with the same species IgG isotype non-immune serum.

The results are summarized in Table 2 with examples in FIG. 9.

TABLE 2

Tissue distribution of human calcium channel $\alpha_2\delta$-4 subunit determined by immunohistochemistry

| Tissue | Cell type | Protein level |
|---|---|---|
| Adrenal | Medulla | +/++ |
| Pituitary | Basophiles | +++ |
|  | other cell types | – |
| Brain | Neurons | +/+/– |
|  | Astrocytes | – |
|  | Purkinje cells | ++/+ |
|  | Fibers | +/– |
| Breast | Epithelium | +/– |
|  | Fibroblasts | – |
| Heart | Cardiocytes | –/+ |

TABLE 2-continued

Tissue distribution of human calcium channel α₂δ-4 subunit determined by immunohistochemistry

| Tissue | Cell type | Protein level |
|---|---|---|
| gut: all parts | Endothelial | − |
|  | Paneth cells | +++ |
|  | Smooth muscle | − |
|  | Epithelium | − |
| Kidney | Endothelial | −/+ |
|  | Tubules | −/+ |
| Skin | Endothelial | − |
|  | nerve bundle | −/+ |
|  | Epidermis | +/− |
|  | Smooth muscle | − |
| fetal liver | RBC blasts | +++ |
|  | Macrophages | − |
|  | RBCs | Some + |
| Liver | Hepatocytes | +/− |
| Pancreas | Islets | +/− |
|  | Epithelium | −/+ |
|  | Miscl |  |
| Lung | Macrophages | −/+ |
|  | Endothelial | − |
|  | Smooth muscle | − |
|  | Epithelium | − |
| Ovary | Smooth muscle | − |
|  | Epithelium | − |
| Testis | Spermatids | −/+ |
|  | Smooth muscle | −/+ |
| Tonsil | WBCs | − |
|  | Endothelial | −/+ |
| Uterus | Smooth muscle | −/+ |
| Placenta | Endothelial | − |
|  | Epithelium | +/− |
|  | RBCs | +/++ |
| prostate | Epithelium | − |
|  | Smooth muscle | −/+ |
| spleen | Macrophages | +/− |
|  | WBCs | − |
|  | RBCs | ++/+ |
|  | Endothelial | +/++ |
| thyroid | Epithelium | −/+ |

Key:
−: negative;
−/+: negative with hint of labeling,
+: week labeling;
+/++: weak to moderate labeling;
++: moderate labeling;
++/+++: moderate to strong labeling and
+++: strong labeling.

The results suggest a role for the splice variant in specific tissues.

EXAMPLE 12

Binding Assay.

All the following procedures are carried out at 4° C. Cells with stable transfected human calcium channel α₂δ-4 subunit are washed with PBS and suspended in lysis buffer (10 mM Tris-HCl pH7.5, 2 mM EDTA and proteinase inhibitor cocktail). The cells are incubated on ice for 40 minutes followed by brief sonication. The cell debris is removed by centrifuge at 1000×g for 10 minutes, and then the supernatant is centrifuged for 1 hour at 50,000×g. The pellet is resuspended in the lysis buffer and kept in 80° C.

The binding assay is carried out in a final volume of 250 μl containing 50 μg cell membrane, 20 mM of [³H] gabapentin and 10 mM Hepes buffer, pH 7.5. After incubation at room temperature for 45 min, the reaction mixture is filtered onto pre-wetted GF/C membranes and washed five times with ice cold 50 mM Tris buffer, pH 7.5. The filters are then dried and counted in a liquid scintillation counter. For screening novel α₂δ-4 subunit ligand, the ability of the compounds to inhibit [³H] gabapentin binding to α₂δ-4 subunit is determined with the same assay in the presence of the compounds.

What is claimed is:

1. An isolated and purified nucleic acid molecule encoding an α2δ-4 calcium channel subunit protein, said nucleic acid molecule comprising a member selected from the group consisting of:
   (a) a polynucleotide encoding a polypeptide having the full-length sequence of SEQ ID NO: 10;
   (b) a nucleic acid molecule that is fully complementary to the polynucleotide of (a);
   (c) a nucleic acid molecule that encodes a splice variant of a human α2δ-4 calcium channel subunit comprising exon 1B (SEQ ID NO:12) which retains the function of an α2δ-4 calcium channel subunit protein;
   (d) a nucleic acid molecule that encodes a splice variant of a human α2δ-4 calcium channel subunit comprising exon 1B (SEQ ID NO: 12) and exon 37B (SEQ ID NO:14) which retains the function of an α2δ-4 calcium channel subunit protein.

2. Any one of the nucleic acid molecules of claim 1 wherein the polynucleotide is RNA.

3. Any one of the nucleic acid molecules of claim 1 wherein the polynucleotide is DNA.

4. An isolated and purified nucleic acid molecule, having the full-length nucleotide sequence of SEQ ID NO: 9.

5. An expression vector to express an α2δ-4 calcium channel subunit protein in an recombinant host cell, wherein said vector contains a nucleic acid sequence encoding a polypeptide having the full-length sequence of SEQ ID NO:10.

6. An isolated recombinant host cell containing an expression vector of claim 5.

7. A method for expressing an α2δ-4 calcium channel subunit protein in an recombiant host cell, comprising the steps of:
   (a) introducing an expression vector capable of encoding a polypeptide having the full-length sequence of SEQ ID NO:10 into a cell; and
   (b) culturing the cells under conditions that allow expression of said polypeptide from the expression vector.

* * * * *

SEQUENCE LISTING

<160> NUMBER OF SEQ ID NOS: 14

<210> SEQ ID NO 1
<211> LENGTH: 27
<212> TYPE: DNA

```
<213> ORGANISM: Artificial Sequence
<220> FEATURE:
<223> OTHER INFORMATION: Description of Artificial Sequence:
      oligonucleotide

<400> SEQUENCE: 1 cagggggctgg gctgcactgt ggtggtg                                    27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
ctctcgggac ctcttggaga tcagaat                                     27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ccatcctaat acgactcact atagggc                                     27

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
actcactata gggctcgagc ggc                                         23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
caggctctga gcctgcgagc tgag                                        24

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
atgtcgtggt cgtggttgat gaccat                                      26

<210> SEQ ID NO 7
<211> LENGTH: 17
<212> TYPE: PRT
<213> ORGANISM: Artificial Sequence
```

```
<220> FEATURE:
<223> OTHER INFORMATION: Description of Artificial Sequence: synthetic
      peptide

<400> SEQUENCE: 7

Lys Val Ser Asp Arg Lys Phe Leu Thr Pro Glu Asp Glu Ala Ser Val
 1               5                  10                  15
Cys

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Arg Val Glu Ala Asp Arg Gly Trp Ala Gly Phe Ser Ser Pro Asn Pro
 1               5                  10                  15
Leu Cys

<210> SEQ ID NO 9
<211> LENGTH: 3486
<212> TYPE: DNA
<213> ORGANISM: Homo sapiens

<400> SEQUENCE: 9
caggtacatt cagcagagcc caagtctgcc actctccaac cagaggccct ggaagcttgg      60
ggtcaagctc agtcctgggc tcgtcagccc ggccccacaa ccctcagcag agaacctgc     120 cgaggacatt cagcacacag cagtgcagcc gctgggtcct gagggttctc cgcgtctcct    180
gcccaggcca tggctgtagc tttagggaca aggaggaggg acagagtgaa gctatgggct    240
gacaccttcg gcggggacct gtataacact gtgaccaaat actcaggctc tctcttgctg    300
cagaagaagt acaaggatgt ggagtccagt ctgaagatcg aggaggtgga tggcttggag    360
ctggtgagga agttctcaga ggacatggag aacatgctgc ggaggaaagt cgaggcggtc    420
cagaatctgg tggaagctgc cgaggaggcc gacctgaacc acgaattcaa tgaatccctg    480
gtgttcgact attacaactc ggtcctgatc aacgagaggg acgagaaggg caacttcgtg    540
gagctgggcg ccgagttcct cctggagtcc aatgctcact tcagcaacct gccggtgaac    600
acctccatca gcagcgtgca gctgcccacc aacgtgtaca caaagaccc agatatttta     660 aatggagtct acatgtctga agccttgaat gctgtcttcg tggagaactt ccagagagac    720
ccaacgttga cctggcaata ttttggcagt gcaactggat tcttcaggat ctatccaggt    780
ataaaatgga cacctgatga gaatggagtc attactttg actgccgaaa ccgcggctgg    840
tacattcaag ctgctacttc tcccaaggac atagtgattt tggtggacgt gagcggcagt    900 atgaagggc tgaggatgac tattgccaag cacaccatca ccaccatctt ggacaccctg    960
ggggagaatg acttcgttaa tatcatagcg tacaatgact acgtcccatta catcgagcct   1020 tgttttaaag ggatcctcgt ccaggcggac cgagacaatc gagagcattt caaactgctg    1080
gtggaggagt tgatggtcaa aggtgtgggg tcgtggacc aagccctgag agaagccttc    1140
cagatcctga agcagttcca agaggccaag caaggaagcc tctgcaacca ggccatcatg    1200
ctcatcagcg acggcgccgt ggaggactac gagccggtgt tgagaagta taactggcca    1260 gactgtaagg tccgagtttt cacttacctc attgggagag aagtgtcttt tgctgaccgc    1320
```

-continued

```
atgaagtgga ttgcatgcaa caacaaaggc tactacacgc agatctcaac gctggcggac   1380
acccaggaga acgtgatgga atacctgcac gtgctcagcc gccccatggt catcaaccac   1440
gaccacgaca tcatctggac agaggcctac atggacagca agctcctcag ctcgcaggct   1500
cagagcctga cactgctcac cactgtggcc atgccagtct tcagcaagaa gaacgaaacg   1560
cgatcccatg gcattctcct gggtgtggtg ggctcagatg tggccctgag agagctgatg   1620
aagctggcgc cccggtacaa gcttggagtg cacggatacg cctttctgaa caccaacaat   1680
ggctacatcc tctcccatcc cgacctccgg cccctgtaca gagagggaa gaaactaaaa   1740 cccaaaccta actacaacag tgtggatctc tccgaagtgg agtgggaaga ccaggctgaa   1800
tctctgagaa cagccatgat caatagggaa acaggtactc tctcgatgga tgtgaaggtt   1860
ccgatggata agggaagcg agttctttc ctgaccaatg actacttctt cacgacatc    1920 agcgacaccc ctttcagttt gggggcggtg ctgtcccggg ccacggaga atacatcctt   1980 ctggggaaca cgtctgtgga agaaggcctg catgacttgc ttcacccaga cctggccctg   2040
gccggtgact ggatctactg catcacagat attgacccag accaccggaa gctcagccag   2100
ctagaggcca tgatccgctt cctcaccagg aaggacccag acctggagtg tgacgaggag   2160
ctggtccggg aggtgctgtt tgacgcggtg gtgacagccc ccatggaagc ctactggaca   2220
gcgctggccc tcaacatgtc cgaggagtct gaacacgtgg tggacatggc cttcctgggc   2280
acccgggctg gcctcctgag aagcagcttg ttcgtgggct ccgagaaggt ctccgacagg   2340
aagttcctga cacctgagga cgaggccagc gtgttcaccc tggaccgctt cccgctgtgg   2400
taccgccagg cctcagagca tcctgctggc agcttcgtct tcaacctccg ctgggcagaa   2460
ggaccagaaa gtgcgggtga acccatggtg gtgacggcaa gcacagctgt ggcggtgacc   2520
gtggacaaga ggacagccat tgctgcagcc gcgggcgtcc aaatgaagct ggaattcctc   2580
cagcgcaaat tctgggcggc aacgcggcag tgcagcactg tggatgggcc gtacacacag   2640
agctgcgagg acagtgatct ggactgcttc gtcatcgaca caacggggtt cattctgatc   2700
tccaagaggt cccgagagac gggaagattt ctggggagg tggatggtgc tgtcctgacc   2760
cagctgctca gcatgggggt gttcagccaa gtgactatgt atgactatca ggccatgtgc   2820
aaaccctcga gtcaccacca cagtgcagcc cagcccctgg tcagcccaat ttctgccttc   2880
ttgacggcga ccaggtggct gctgcaggag ctggtgctgt tcctgctgga gtggagtgtc   2940
tggggctcct ggtacgacag aggggccgag gccaaaagtg tcttccatca ctcccacaaa   3000
cacaagaagc aggacccgct gcagccctgc gacacggagt accccgtgtt cgtgtaccag   3060
ccggccatcc gggaggccaa cgggatcgtg gagtgcgggc cctgccagaa ggtatttgtg   3120
gtgcagcaga ttcccaacag taacctcctc ctcctggtga cagacccac ctgtgactgc    3180 agcatcttcc caccagtgct gcaggaggcg acagaagtca aatataatgc ctctgtcaaa   3240
tgtgaccgga tgcgctccca gaagctccgc cggcgaccag actcctgcca cgccttccat   3300
ccagaggtgc gggttgaggc ggatcgaggg tgggctggat tttcatcccc aaaccctctg   3360
tgcctgggtc tgtgccccctg cagacaggag catatatggga tgccaatgaa cacacctgtg   3420
cctgtgcttc tcgggggaaa cattcgcgtt tatgccctgt gacactgtga tataataaga   3480
aacaga                                                             3486
```

<210> SEQ ID NO 10
<211> LENGTH: 1090
<212> TYPE: PRT
<213> ORGANISM: Homo sapiens

<400> SEQUENCE: 10

```
Met Ala Val Ala Leu Gly Thr Arg Arg Arg Asp Arg Val Lys Leu Trp
 1               5                  10                  15

Ala Asp Thr Phe Gly Gly Asp Leu Tyr Asn Thr Val Thr Lys Tyr Ser
             20                  25                  30

Gly Ser Leu Leu Leu Gln Lys Lys Tyr Lys Asp Val Glu Ser Ser Leu
         35                  40                  45

Lys Ile Glu Glu Val Asp Gly Leu Glu Leu Val Arg Lys Phe Ser Glu
     50                  55                  60

Asp Met Glu Asn Met Leu Arg Arg Lys Val Glu Ala Val Gln Asn Leu
 65                  70                  75                  80

Val Glu Ala Ala Glu Ala Asp Leu Asn His Glu Phe Asn Glu Ser
             85                  90                  95

Leu Val Phe Asp Tyr Tyr Asn Ser Val Leu Ile Asn Glu Arg Asp Glu
             100                 105                 110

Lys Gly Asn Phe Val Glu Leu Gly Ala Glu Phe Leu Leu Glu Ser Asn
         115                 120                 125

Ala His Phe Ser Asn Leu Pro Val Asn Thr Ser Ile Ser Ser Val Gln
     130                 135                 140

Leu Pro Thr Asn Val Tyr Asn Lys Asp Pro Asp Ile Leu Asn Gly Val
145                 150                 155                 160

Tyr Met Ser Glu Ala Leu Asn Ala Val Phe Val Glu Asn Phe Gln Arg
             165                 170                 175

Asp Pro Thr Leu Thr Trp Gln Tyr Phe Gly Ser Ala Thr Gly Phe Phe
             180                 185                 190

Arg Ile Tyr Pro Gly Ile Lys Trp Thr Pro Asp Glu Asn Gly Val Ile
         195                 200                 205

Thr Phe Asp Cys Arg Asn Arg Gly Trp Tyr Ile Gln Ala Ala Thr Ser
     210                 215                 220

Pro Lys Asp Ile Val Ile Leu Val Asp Val Ser Gly Ser Met Lys Gly
225                 230                 235                 240

Leu Arg Met Thr Ile Ala Lys His Thr Ile Thr Thr Ile Leu Asp Thr
             245                 250                 255

Leu Gly Glu Asn Asp Phe Val Asn Ile Ile Ala Tyr Asn Asp Tyr Val
             260                 265                 270

His Tyr Ile Glu Pro Cys Phe Lys Gly Ile Leu Val Gln Ala Asp Arg
         275                 280                 285

Asp Asn Arg Glu His Phe Lys Leu Leu Val Glu Glu Leu Met Val Lys
     290                 295                 300

Gly Val Gly Val Val Asp Gln Ala Leu Arg Glu Ala Phe Gln Ile Leu
305                 310                 315                 320

Lys Gln Phe Gln Glu Ala Lys Gln Gly Ser Leu Cys Asn Gln Ala Ile
             325                 330                 335

Met Leu Ile Ser Asp Gly Ala Val Glu Asp Tyr Glu Pro Val Phe Glu
             340                 345                 350

Lys Tyr Asn Trp Pro Asp Cys Lys Val Arg Val Phe Thr Tyr Leu Ile
         355                 360                 365

Gly Arg Glu Val Ser Phe Ala Asp Arg Met Lys Trp Ile Ala Cys Asn
     370                 375                 380

Asn Lys Gly Tyr Tyr Thr Gln Ile Ser Thr Leu Ala Asp Thr Gln Glu
385                 390                 395                 400

Asn Val Met Glu Tyr Leu His Val Leu Ser Arg Pro Met Val Ile Asn
```

-continued

```
                405                 410                 415
His Asp His Asp Ile Ile Trp Thr Glu Ala Tyr Met Asp Ser Lys Leu
            420                 425                 430

Leu Ser Ser Gln Ala Gln Ser Leu Thr Leu Leu Thr Thr Val Ala Met
            435                 440                 445

Pro Val Phe Ser Lys Lys Asn Glu Thr Arg Ser His Gly Ile Leu Leu
            450                 455                 460

Gly Val Val Gly Ser Asp Val Ala Leu Arg Glu Leu Met Lys Leu Ala
465                 470                 475                 480

Pro Arg Tyr Lys Leu Gly Val His Gly Tyr Ala Phe Leu Asn Thr Asn
            485                 490                 495

Asn Gly Tyr Ile Leu Ser His Pro Asp Leu Arg Pro Leu Tyr Arg Glu
            500                 505                 510

Gly Lys Lys Leu Lys Pro Lys Pro Asn Tyr Asn Ser Val Asp Leu Ser
            515                 520                 525

Glu Val Glu Trp Glu Asp Gln Ala Glu Ser Leu Arg Thr Ala Met Ile
            530                 535                 540

Asn Arg Glu Thr Gly Thr Leu Ser Met Asp Val Lys Val Pro Met Asp
545                 550                 555                 560

Lys Gly Lys Arg Val Leu Phe Leu Thr Asn Asp Tyr Phe Phe Thr Asp
            565                 570                 575

Ile Ser Asp Thr Pro Phe Ser Leu Gly Ala Val Leu Ser Arg Gly His
            580                 585                 590

Gly Glu Tyr Ile Leu Leu Gly Asn Thr Ser Val Glu Glu Gly Leu His
            595                 600                 605

Asp Leu Leu His Pro Asp Leu Ala Leu Ala Gly Asp Trp Ile Tyr Cys
            610                 615                 620

Ile Thr Asp Ile Asp Pro Asp His Arg Lys Leu Ser Gln Leu Glu Ala
625                 630                 635                 640

Met Ile Arg Phe Leu Thr Arg Lys Asp Pro Asp Leu Glu Cys Asp Glu
            645                 650                 655

Glu Leu Val Arg Glu Val Leu Phe Asp Ala Val Val Thr Ala Pro Met
            660                 665                 670

Glu Ala Tyr Trp Thr Ala Leu Ala Leu Asn Met Ser Glu Glu Ser Glu
            675                 680                 685

His Val Val Asp Met Ala Phe Leu Gly Thr Arg Ala Gly Leu Leu Arg
            690                 695                 700

Ser Ser Leu Phe Val Gly Ser Glu Lys Val Ser Asp Arg Lys Phe Leu
705                 710                 715                 720

Thr Pro Glu Asp Glu Ala Ser Val Phe Thr Leu Asp Arg Phe Pro Leu
            725                 730                 735

Trp Tyr Arg Gln Ala Ser Glu His Pro Ala Gly Ser Phe Val Phe Asn
            740                 745                 750

Leu Arg Trp Ala Glu Gly Pro Glu Ser Ala Gly Glu Pro Met Val Val
            755                 760                 765

Thr Ala Ser Thr Ala Val Ala Val Thr Val Asp Lys Arg Thr Ala Ile
            770                 775                 780

Ala Ala Ala Ala Gly Val Gln Met Lys Leu Glu Phe Leu Gln Arg Lys
785                 790                 795                 800

Phe Trp Ala Ala Thr Arg Gln Cys Ser Thr Val Asp Gly Pro Tyr Thr
            805                 810                 815

Gln Ser Cys Glu Asp Ser Asp Leu Asp Cys Phe Val Ile Asp Asn Asn
            820                 825                 830
```

Gly Phe Ile Leu Ile Ser Lys Arg Ser Arg Glu Thr Gly Arg Phe Leu
                835                 840                 845

Gly Glu Val Asp Gly Ala Val Leu Thr Gln Leu Leu Ser Met Gly Val
            850                 855                 860

Phe Ser Gln Val Thr Met Tyr Asp Tyr Gln Ala Met Cys Lys Pro Ser
865                 870                 875                 880

Ser His His His Ser Ala Ala Gln Pro Leu Val Ser Pro Ile Ser Ala
                885                 890                 895

Phe Leu Thr Ala Thr Arg Trp Leu Leu Gln Glu Leu Val Leu Phe Leu
            900                 905                 910

Leu Glu Trp Ser Val Trp Gly Ser Trp Tyr Asp Arg Gly Ala Glu Ala
            915                 920                 925

Lys Ser Val Phe His His Ser His Lys His Lys Gln Asp Pro Leu
            930                 935                 940

Gln Pro Cys Asp Thr Glu Tyr Pro Val Phe Val Tyr Gln Pro Ala Ile
945                 950                 955                 960

Arg Glu Ala Asn Gly Ile Val Glu Cys Gly Pro Cys Gln Lys Val Phe
                965                 970                 975

Val Val Gln Gln Ile Pro Asn Ser Asn Leu Leu Leu Val Thr Asp
            980                 985                 990

Pro Thr Cys Asp Cys Ser Ile Phe Pro Pro Val Leu Gln Glu Ala Thr
            995                 1000                1005

Glu Val Lys Tyr Asn Ala Ser Val Lys Cys Asp Arg Met Arg Ser Gln
    1010                1015                1020

Lys Leu Arg Arg Arg Pro Asp Ser Cys His Ala Phe His Pro Glu Val
1025                1030                1035                1040

Arg Val Glu Ala Asp Arg Gly Trp Ala Gly Phe Ser Pro Asn Pro
            1045                1050                1055

Leu Cys Leu Gly Leu Cys Pro Cys Arg Gln Glu His Ile Gly Met Pro
                1060                1065                1070

Met Asn Thr Pro Val Pro Val Leu Leu Gly Gly Asn Ile Arg Val Tyr
            1075                1080                1085

Ala Leu
    1090

<210> SEQ ID NO 11
<211> LENGTH: 188
<212> TYPE: DNA
<213> ORGANISM: Homo sapiens

<400> SEQUENCE: 11
gccaccatgc ctgcaactcc caacttcctc gcaaaccca gctccagcag ccgctggatt      60
tggattcccc tccagccaat gcccgtggcc tgggcctttg tgcagaagac ctcggccctc     120
ctgtggctgc tgcttctagg cacctccctg tccctgcgt ggggacaggc caagattcct      180
ctggaaac                                                              188

<210> SEQ ID NO 12
<211> LENGTH: 58
<212> TYPE: PRT
<213> ORGANISM: Homo sapiens

<400> SEQUENCE: 12

Met Pro Ala Thr Pro Asn Phe Leu Ala Asn Pro Ser Ser Ser Arg
  1               5                  10                  15

```
Trp Ile Pro Leu Gln Pro Met Pro Val Ala Trp Ala Phe Val Gln Lys
            20                  25                  30

Thr Ser Ala Leu Leu Trp Leu Leu Leu Gly Thr Ser Leu Ser Pro
            35                  40                  45

Ala Trp Gly Gln Ala Lys Ile Pro Leu Glu
        50                  55

<210> SEQ ID NO 13
<211> LENGTH: 105
<212> TYPE: DNA
<213> ORGANISM: Homo sapiens

<400> SEQUENCE: 13
gagaatgccc aggactgcgg cggcgcctcg gacacctcag cctcgccgcc cctactcctg      60
ctgcctgtgt gtgcctgggg gctactgccc caactcctgc ggtga                    105

<210> SEQ ID NO 14
<211> LENGTH: 35
<212> TYPE: PRT
<213> ORGANISM: Homo sapiens

<400> SEQUENCE: 14

Glu Asn Ala Gln Asp Cys Gly Gly Ala Ser Asp Thr Ser Ala Ser Ser
 1               5                  10                  15

Pro Pro Leu Leu Leu Pro Val Cys Ala Trp Gly Leu Leu Pro Gln
            20                  25                  30

Leu Leu Arg
        35
```